(12) United States Patent
Neidell

(10) Patent No.: US 12,165,403 B2
(45) Date of Patent: *Dec. 10, 2024

(54) METHODS FOR DIGITAL IMAGING OF LIVING TISSUE

(71) Applicant: Norman Neidell, Houston, TX (US)

(72) Inventor: Norman Neidell, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/236,305

(22) Filed: Aug. 21, 2023

(65) Prior Publication Data

US 2024/0265696 A1 Aug. 8, 2024

Related U.S. Application Data

(63) Continuation of application No. 17/391,275, filed on Aug. 2, 2021, now Pat. No. 11,734,921, which is a
(Continued)

(51) Int. Cl.
| | |
|---|---|
| *G06V 20/00* | (2022.01) |
| *A61B 5/05* | (2021.01) |
| *G01V 1/00* | (2024.01) |
| *G01V 1/28* | (2006.01) |
| *G01V 1/30* | (2006.01) |

(Continued)

(52) U.S. Cl.
CPC ............... *G06V 20/00* (2022.01); *A61B 5/05* (2013.01); *G01V 1/005* (2013.01); *G01V 1/282* (2013.01); *G01V 1/284* (2013.01); *G01V 1/30* (2013.01); *G01V 1/302* (2013.01); *G01V 1/345* (2013.01); *G03H 1/0808* (2013.01); *G06F 18/22* (2023.01); *G06T 7/0002* (2013.01); *G06T 7/0014* (2013.01); *G06T 11/00* (2013.01); *G01V 2210/1234* (2013.01); *G03H 2001/0033* (2013.01); *G06T 2207/30004* (2013.01); *G06T 2207/30168* (2013.01); *G06V 2201/03* (2022.01)

(58) Field of Classification Search
CPC ............. G06K 9/00624; G06K 9/6215; G03H 1/0808; G06T 7/0002; G06T 11/00; G06T 2001/0033; G06T 2207/30168
See application file for complete search history.

(56) References Cited

U.S. PATENT DOCUMENTS

| | | | |
|---|---|---|---|
| 2002/0131551 A1* | 9/2002 | Johnson | ................... G01S 13/89 378/62 |
| 2012/0095689 A1* | 4/2012 | Kostov | ..................... G01V 1/28 702/14 |
| 2014/0293740 A1* | 10/2014 | Compton | ............... G01V 1/366 367/7 |

* cited by examiner

*Primary Examiner* — Dakshesh D Parikh
(74) *Attorney, Agent, or Firm* — Elliott Law PLLC; Douglas H. Elliott; Nathan Q. Huynh

(57) ABSTRACT

Methods of providing digital images of living tissue that may include: obtaining data of a propagating wavefield through living tissue; obtaining a reference digital image of the living tissue; selecting a holographic computational method of wavefield imaging; selecting a wavefield based on one or more parameters; calculating a sampling ratio by dividing a number of data samples in the data subset by a number of image samples in the data subset; decimating the data subset; generating a new digital image based on the selected holographic computational method of imaging, the decimated data subset, and parameters corresponding to the data subset; and determining a quantitative difference measure between the reference digital image and the new digital image based on the changing of one or more parameters selected from the group consisting of field sampling, imaging sampling, and image quality.

19 Claims, 19 Drawing Sheets

Related U.S. Application Data continuation of application No. 16/905,114, filed on Jun. 18, 2020, now Pat. No. 11,080,856.

(60) Provisional application No. 62/863,123, filed on Jun. 18, 2019.

(51) Int. Cl.
*G01V 1/34* (2006.01)
*G03H 1/00* (2006.01)
*G03H 1/08* (2006.01)
*G06F 18/22* (2023.01)
*G06T 7/00* (2017.01)
*G06T 11/00* (2006.01)

Texas Glenrose Reef
Cretaceous Section 2D Data 1980's

Conventional Display

Composite Inversion

METHODS FOR DIGITAL IMAGING OF LIVING TISSUE

CROSS REFERENCE TO RELATED APPLICATIONS

This application is a continuation of U.S. Nonprovisional application Ser. No. 17/391,275, filed on Aug. 2, 2021, which claims benefit to U.S. Nonprovisional application Ser. No. 16/905,114, filed on Jun. 18, 2020, which is a continuation of U.S. Provisional Application 62/863,123, filed on Jun. 18, 2019; and this application hereby incorporates herein U.S. Nonprovisional application Ser. No. 17/391,275 and 16/905,114 and U.S. Provisional Application 62/863,123 as if set forth herein in their entireties.

BACKGROUND

1. Field of Inventions

The field of this application and any resulting patent is digital imaging of living tissue.

2. Description of Related Art

Various methods of providing digital images of living tissue have been proposed and utilized, including the methods and systems disclosed in the references appearing on the face of this patent. However, these methods and systems lack all the steps or features of the methods and devices covered by the patent claims below. Furthermore, the methods and systems covered by at least some of the claims of this issued patent may solve many of the problems that prior art methods and systems have failed to solve. Also, the methods and systems covered by at least some of the claims of this patent may have benefits that would be surprising and unexpected to a person of ordinary skill in the art based on the prior art existing at the time of the inventions set forth in one or more of the claims herein.

SUMMARY

Disclosed herein are methods of digital imaging of living tissue that may include: 1) obtaining wavefield data representing recordings of a propagating wavefield through living tissue; 2) obtaining a reference digital image of a portion or all of the living tissue generated from the wavefield data, wherein the reference image may have a reference sampling ratio and a reference image quality value; 3) selecting a holographic computational method of imaging the wavefield data from a group consisting of the Kirchhoff diffraction stacking method, the Kirchhoff wave front "smear" method, wavefield synthesis, and wave equation-based methods; 4) selecting a data subset from the wavefield data based on one or more parameters selected from the group consisting of field sampling, imaging sampling, and image quality; 5) calculating a sampling ratio by dividing a number of data samples in the data subset by a number of image samples in the data subset; 6) decimating the data subset, wherein the decimated data subset may represent a sampling ratio less than the reference sampling ratio; 7) generating a new digital image based on the selected holographic computational method of imaging, the decimated data subset, and parameters corresponding to the data subset selected from the group consisting of legal parameters, operational parameters, financial parameters, and safety parameters, wherein the new digital image may have a new image quality value greater than the reference image quality value; and 8) determining a quantitative difference measure between the reference digital image and the new digital image based on the changing of one or more parameters selected from the group consisting of field sampling, imaging sampling, and image quality.

DETAILED DESCRIPTION

1. Introduction

Figure 1:
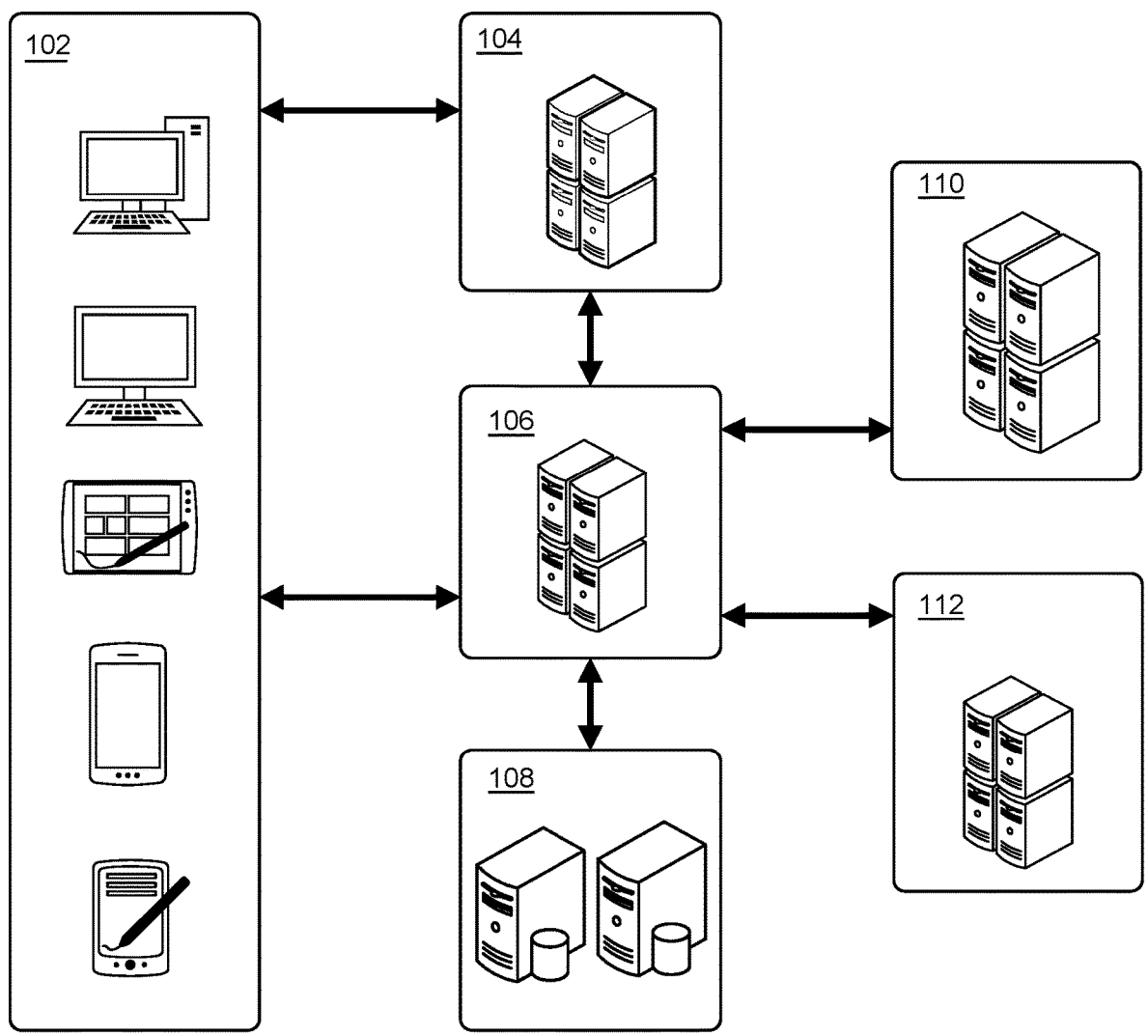
FIG. 1 is a schematic diagram of an imaging system.

A detailed description will now be provided. The purpose of this detailed description, which includes the drawings, is to satisfy the statutory requirements of 35 U.S.C. § 112. For example, the detailed description includes a description of the inventions disclosed herein and sufficient information that would enable a person having ordinary skill in the art to make and use the inventions. In the figures, like elements are generally indicated by like reference numerals regardless of the view or figure in which the elements appear. The figures are intended to assist the description and to provide a visual representation of certain aspects of the subject matter described herein. The figures are not all necessarily drawn to scale, nor do they show all the structural details of the systems, nor do they limit the scope of the disclosure herein.

2. Selected Definitions

Certain claims include one or more of the following terms which, as used herein, are expressly defined below.

It will be apparent that the various terms identified and/or defined below may be embodied in methods, systems, and/or non-transient, computer-readable media (CRM), e.g., as part of a set of machine-readable instructions (object code) residing in some type of computer hardware, e.g., processors or memory. The various ways to use the items represented by the terms discussed below, and to implement the equations, calculations, and algorithms described herein, will be known or can otherwise be determined by persons skilled in the art of computer programming based on this patent application disclosure, particularly those who are familiar with writing computer programs, including computer programs relating to optimizing digital imaging. Also, the items discussed below, may be implemented in a variety of different types of computer programs using any one of a number of different programming languages; and the methods, systems, and CRM are not limited to any particular computer program or programming language.

The term "attribute" as used herein is defined as a quality, property, or characteristic of something.

The term "acquisition" as used herein is defined as an act of.

The term "data" as used herein is defined as information, e.g., information associated with one or more nouns, e.g., an entity. A first portion of data may have a relationship with a second portion of data.

The term "database" as used herein is defined as a structured set of data, e.g., information stored on a digital storage medium or a computer configured for rapid storage, grouping, query, manipulation, and/or presentation of the data. A database may have one or more structures, e.g., tables, views, or synonyms. A database may have one or more structures configured for grouping and/or presentation of data. A database may have instructions, e.g., stored procedures, configured to rapidly read, fetch, insert, update, and/or delete data in a table.

The term "digital" as used herein is defined as a series of numbers, e.g., 0's and 1's.

The term "digital image" as used herein is defined as a numeric representation of one or more properties of a two-dimensional area or three-dimensional volume.

The term "exemplary" is used exclusively herein to mean "serving as an example, instance, or illustration." Anything, including any embodiment, structure, element, or step, described herein as exemplary, is not to be construed as preferred or advantageous over other embodiments, structures, elements, steps, etc.

The term "field sampling" as used herein is defined as data representing an identifier and/or position of a detector used to detect a propagating wavefield.

The terms "he," "she," "they," and any other personal pronouns as used herein refer to any gender interchangeably. For example, all uses of "he" encompasses "she" as well.

The term "holographic computational method" as used herein is defined as a method of processing encoded data representing wavefields propagating within a propagation volume. The encoded data may include holographic encoded data. Holographic computational methods may include, e.g., the Kirchhoff diffraction stacking method, the Kirchhoff wavefront smear method, wavefield synthesis, and wave equation-based methods.

The term "identifier" as used herein is defined as one or more data values that uniquely identify and/or distinguish a record from any other record stored in a table. An identifier may be referred to as a primary key.

The term "image sampling" as used herein is defined as a number of pixels or voxels defining a digital image or volume.

The term "optimize" as used herein means to improve. For example, optimizing production of a digital image may include one or more steps to rearrange, rewrite, and/or decimate data and/or operations, to improve efficiency of the production. Optimize may include a step to calculate a value of a distance measured in a multivariate criteria space. A multivariate criteria space may include any one or more of a number of components of technical parameters and business environment parameters. Technical parameters may include, e.g., computational methods, field samplings, image samplings, and image quality. Business environment parameters may environmental parameters, legal parameters, operational parameters, financial parameters, and safety parameters.

The term "parameter" as used herein is defined as a variable or argument, e.g., used in a function or subroutine. Types of parameters may include, e.g., technical parameters and business environment parameter. Technical parameters may include, e.g., computational methods parameters, field sampling parameters, image sampling parameters, and image quality parameters. Business environment parameter may include, e.g., legal parameters, operational parameters, financial parameters, and safety parameters. A parameter may have a value, e.g., number.

The term "quantitative difference distance measure" as used herein is defined as a multivariate value, e.g., quantity. A set of quantitative difference distance measure may be ranked.

The term "sampling ratio" as used herein is defined as a ratio of a sample size or a population size. For example, sampling ratio of wavefield recordings may be equal to a number of data samples in a data subset divided by a number of image samples in the data subset.

The term "propagation volume" as used herein is defined as a portion of a body, structure, or space capable of receiving energy waves, e.g., sound, vibration, or light. A propagation volume may receive a propagating wavefield. A propagation volume may be animate or inanimate. For example, an animate propagation volume may be a portion of a human body, e.g., head, torso, or limbs, or some other living tissue, or formerly living tissue. Thus, the methods disclosed herein have medical applicability in which a propagation volume is some portion of the human body such as the brain, a breast, or a lung. An inanimate propagation volume may be a geophysical volume of the earth, e.g., underground oil field, ocean bed, or bedrock. Accordingly, oil and gas exploration methods are disclosed that include the providing of digital imaging in which the propagation volume is a geophysical volume. Also disclosed herein are methods for identifying subterranean tunnels, including caverns, mineshafts, or buried conduits including the providing of digital images. Additionally, an inanimate propagation volume may be a portion of a celestial body, e.g., asteroid, comet, moon, or planet. Accordingly, methods for identifying flying objects are disclosed where the propagation volume is some non-solid space above the earth's surface, which may be any part of the atmosphere, such that the flying objects may be aircraft such as drones or airplanes, but the propagation volume may also be above the earth's atmosphere, including outer space, wherein electromagnetic signals can be used to form images of flying objects such as manned bodies or projectiles. Types of propagation volume may include, e.g., a geophysical volume and a Cartesian volume. A "geophysical volume" may be a portion of the earth having a length, width, and depth. A "Cartesian volume" may have positions within it that can described by an orthogonal coordinate system, which may be denoted as X, Y, and Z, for example. A propagation volume may be represented digitally, e.g., as an image volume and/or data volume. An image volume may incorporate all or some representation of a propagation volume in which some property related to the propagation volume is represented visually as an image. Also, a data volume or data capture may be an organized representation of digitally recorded wavefield data for computations. A data volume may be coincident in whole or part with the propagation volume and/or the image volume. Entries within a data volume may be of matrix or vector nature, and multivalued as well in depending on source and receiver locations.

The term "receiver" as used herein is defined as a device for receiving and/or recording propagating wavefields.

The term "source" as used herein is defined as a device for discharging energy into a propagation volume.

The term "table" as used herein is defined as a logical structure, e.g., grouping, of data in a database configured for rapid grouping, query, and/or manipulation of the data. A table may represent a real-world group of things, e.g., signal source, signal receiver, voxel, question, and/or answer. Each thing may have attributes or characteristics, e.g., dimension or direction. Each thing may be represented by a record in a table. Each attribute of each thing may be represented by a field in the table. Each record on each data table may or, in some cases, may not have data that must conform to the rules of a table definition. A field for each attribute must conform to certain data type constraints, e.g., always be a numeral, a string of letters and/or characters, or a binary value. Additionally, a field for each attribute must conform to certain value or format constraints, e.g., be non-repetitive, be uniquely named, and/or always have some value or a default value. Each record may be referred to as a row. Each field may be referred to as a column. A first record in a first table may be associated with, e.g., related or linked to, a second record in a second table via a foreign key, e.g., one or more common fields.

The term "value" as used herein is defined as one or more symbols assigned to and identifying a quality, characteristic, and/or quantity of a thing, e.g., entity. A symbol may be, e.g., a number, a letter, a picture, a character, or anything perceptible. A value may be stored in a field in a table of a database. The term "value" covers all of those different types of values, and others as well. In the context of certain methods, systems, and CRM described herein, any "value" that is used, whether provided or determined, e.g., calculated, may take the form of a value that is part of the instructions of a computer program, and also can be an electronic value stored in computer memory or on some CRM.

The term "voxel" as used herein is defined as an array of elements of volume that constitute a notional three-dimensional volume. A voxel may represent a portion of a propagation volume. A voxel may be cubic in nature. A voxel may include attributes, e.g., size, dimensions, location, to constitute a component of an image volume. One or more interactions between a voxel and a digitized wavefield may be simulated. A voxel may be used to approximate one or more properties of a three-dimensional volume. A voxel may have a unique identifier having a source identifier, a receiver identifier, and/or time.

The term "wavefield" as used herein is defined as a disturbance, e.g., propagating energy, within a propagation volume. A wavefield may be generated by a wavefield source. A wavefield may be recorded by a receiver. The term "propagating wavefield" as used herein is defined as a disturbance propagating in at least one spatial coordinate of a propagation volume.

3. Certain Specific Embodiments

Disclosed herein are methods of digital imaging of living tissue that may include: 1) obtaining wavefield data representing recordings of a propagating wavefield through living tissue; 2) obtaining a reference digital image of a portion or all of the living tissue generated from the wavefield data, wherein the reference image may have a reference sampling ratio and a reference image quality value; 3) selecting a holographic computational method of imaging the wavefield data from a group consisting of the Kirchhoff diffraction stacking method, the Kirchhoff wave front "smear" method, wavefield synthesis, and wave equation-based methods; 4) selecting a data subset from the wavefield data based on one or more parameters selected from the group consisting of field sampling, imaging sampling, and image quality; 5) calculating a sampling ratio by dividing a number of data samples in the data subset by a number of image samples in the data subset; 6) decimating the data subset, wherein the decimated data subset may represent a sampling ratio less than the reference sampling ratio; 7) generating a new digital image based on the selected holographic computational method of imaging, the decimated data subset, and parameters corresponding to the data subset selected from the group consisting of legal parameters, operational parameters, financial parameters, and safety parameters, wherein the new digital image may have a new image quality value greater than the reference image quality value; and 8) determining a quantitative difference measure between the reference digital image and the new digital image based on the changing of one or more parameters selected from the group consisting of field sampling, imaging sampling, and image quality.

In addition, disclosed herein are methods for identifying a flying object using digital imaging that may include: 1) obtaining wavefield data representing recordings of a propagating wavefield through a propagating volume that may include a volume above the earth's surface; 2) obtaining a reference digital image of a portion or all of the propagating volume generated from the wavefield data, wherein the reference image may have a reference sampling ratio and a reference image quality value; 3) selecting a holographic computational method of imaging the wavefield data from a group consisting of the Kirchhoff diffraction stacking method, the Kirchhoff wave front "smear" method, wavefield synthesis, and wave equation-based methods; 4) selecting a data subset from the wavefield data based on one or more parameters selected from the group consisting of field sampling, imaging sampling, and image quality; 5) calculating a sampling ratio by dividing a number of data samples in the data subset by a number of image samples in the data subset; 6) decimating the data subset, wherein the decimated data subset may represent a sampling ratio less than the reference sampling ratio; 7) generating a new digital image that may include a flying object passing through at least a portion of the propagating volume based on the selected holographic computational method of imaging the decimated data subset, and parameters corresponding to the data subset selected from the group consisting of environmental parameters, legal parameters, operational parameters, financial parameters, and safety parameters, wherein the new digital image has a new image quality value greater than the reference image quality value; and 8) determining a quantitative difference measure between the reference digital image and the new digital image based on the changing of one or more parameters selected from the group consisting of field sampling, imaging sampling, and image quality.

Also, disclosed herein are methods for identifying a subterranean tunnel using digital imaging that may include: 1) obtaining wavefield data representing recordings of a propagating wavefield through a propagating volume that may include a portion of the earth's subsurface; 2) obtaining a reference digital image of a portion or all of the propagating volume generated from the wavefield data, wherein the reference image may have a reference sampling ratio and a reference image quality value; 3) selecting a holographic computational method of imaging the wavefield data from a group consisting of the Kirchhoff diffraction stacking method, the Kirchhoff wave front "smear" method, wavefield synthesis, and wave equation-based methods; 4) selecting a data subset from the wavefield data based on one or more parameters selected from the group consisting of field sampling, imaging sampling, and image quality; 5) calculating a sampling ratio by dividing a number of data samples in the data subset by a number of image samples in the data subset; 6) decimating the data subset, wherein the decimated data subset may represent a sampling ratio less than the reference sampling ratio; 7) generating a new digital image that may include a subterranean tunnel passing through at least a portion of the propagating volume based on the selected holographic computational method of imaging the decimated data subset, and parameters corresponding to the data subset selected from the group consisting of environmental parameters, legal parameters, operational parameters, financial parameters, and safety parameters, wherein the new digital image has a new image quality value greater than the reference image quality value; 8) determining a quantitative difference measure between the reference digital image and the new digital image based on the changing of one or more parameters selected from the group consisting of field sampling, imaging sampling, and image quality; and 9) identifying the subterranean tunnel.

Additionally, disclosed herein are methods of oil and gas exploration that may include: 1) obtaining wavefield data representing recordings of a propagating wavefield through a geophysical volume; 2) obtaining a reference digital image of a portion or all of the geophysical volume generated from the wavefield data, wherein the reference image may have a reference sampling ratio and a reference image quality value; 3) selecting a holographic computational method of imaging the wavefield data from a group consisting of the Kirchhoff diffraction stacking method, the Kirchhoff wave front "smear" method, wavefield synthesis, and wave equation-based methods; 4) selecting a data subset from the wavefield data based on one or more parameters selected from the group consisting of field sampling, imaging sampling, and image quality; 5) calculating a sampling ratio by dividing a number of data samples in the data subset by a number of image samples in the data subset; 6) decimating the data subset, wherein the decimated data subset may represent a sampling ratio less than the reference sampling ratio; 7) generating a new digital image based on the selected holographic computational method of imaging, the decimated data subset, and parameters corresponding to the data subset selected from the group consisting of environmental parameters, legal parameters, operational parameters, financial parameters, and safety parameters, wherein the new digital image may have a new image quality value greater than the reference image quality value; and 8) determining a quantitative difference measure between the reference digital image and the new digital image based on changing one or more parameters selected from the group consisting of field sampling, imaging sampling, and image quality.

Further, disclosed herein are methods of providing a digital image of a geophysical volume that may include: 1) obtaining wavefield data representing recordings from a propagating wavefield through the geophysical volume; 2) obtaining at least one reference digital image of a portion or all of the geophysical volume generated from the wavefield data, wherein the reference image has a reference sampling ratio and a reference image quality value; 3) selecting a holographic computational method of imaging the wavefield data; 4) selecting a data subset from the wavefield data based on one or more parameters selected from the group consisting of field sampling, imaging sampling, and image quality; 5) decimating the data subset, wherein the decimated data subset represents a sampling ratio less than the reference sampling ratio; and 6) generating a subsequent digital image based on the selected holographic computational method of imaging, the data subset, and parameters corresponding to the data subset selected from the group consisting of environmental parameters, legal parameters, operational parameters, financial parameters, and safety parameters, wherein the subsequent digital image has a new image quality value greater than the reference image quality value.

Disclosed herein are methods of providing a digital image of a propagation volume that may include: 1) obtaining wavefield data representing recordings from a propagating wavefield through the propagation volume; 2) obtaining at least one reference digital image of a portion or all of the propagation volume generated from the wavefield data, wherein the reference image has a reference sampling ratio and a reference image quality value; 3) selecting a holographic computational method of imaging the wavefield data; 4) selecting a data subset from the wavefield data based on one or more parameters selected from the group consisting of field sampling, imaging sampling, and image quality; 5) decimating the data subset, wherein the decimated data subset represents a sampling ratio less than the reference sampling ratio; and 6) generating a subsequent digital image based on the selected holographic computational method of imaging, the data subset, and parameters corresponding to the data subset selected from the group consisting of environmental parameters, legal parameters, operational parameters, financial parameters, and safety parameters, wherein the subsequent digital image has a new image quality value greater than the reference image quality value.

In any one of the methods disclosed herein, the computational method of imaging the wavefield data is selected from a group consisting of the Kirchhoff diffraction stacking method, the Kirchhoff wave front "smear" method, wavefield synthesis, and wave equation-based methods.

In any one of the methods disclosed herein, the sampling ratio is equal to a number of data samples in the data subset divided by a number of image samples in the data subset.

Any one of the methods disclosed herein may further include determining a difference between the reference digital image and the subsequent digital image based on one or more parameters selected from the group consisting of field sampling, imaging sampling, and image quality.

Any one of the methods disclosed herein may further include determining a quantitative difference measure between the reference digital image and the subsequent digital image based on one or more parameters selected from the group consisting of field sampling, imaging sampling, and image quality.

Any one of the methods disclosed herein may further include implementing an imaging survey on another propagation volume based on a configuration of source array and receiver array corresponding to the data subset.

Any one of the methods disclosed herein may further include positioning on another geophysical volume an array of sources and an array of receivers based on the data subset.

Any one of the methods disclosed herein may further include positioning in another geophysical volume an array of sources and an array of receivers based on the data subset.

Any one of the methods disclosed herein may further include propagating a wavefield through another geophysical volume with an array of sources having a configuration based on the data subset.

Any one of the methods disclosed herein may further include receiving a propagating wavefield from another geophysical volume with an array of receivers having a configuration based on the data subset.

Any one of the methods disclosed herein may further include recording a propagating wavefield from another geophysical volume with an array of receivers having a configuration based on the data subset.

Any one of the methods disclosed herein may further include positioning on another propagation volume an array of sources and an array of receivers based on the data subset.

Any one of the methods disclosed herein may further include positioning in another propagation volume an array of sources and an array of receivers based on the data subset.

Any one of the methods disclosed herein may further include propagating a wavefield through another propagation volume with an array of sources having a configuration based on the data subset.

Any one of the methods disclosed herein may further include receiving a propagating wavefield from another propagation volume with an array of receivers having a configuration based on the data subset.

Any one of the methods disclosed herein may further include recording a propagating wavefield from another propagation volume with an array of receivers having a configuration based on the data subset.

4. Specific Embodiments in the Drawings

The drawings presented herein are for illustrative purposes only and do not limit the scope of the claims. Rather, the drawings are intended to help enable one having ordinary skill in the art to make and use the claimed inventions.

This section addresses specific embodiments of the inventions shown in the drawings, which relate to methods, systems, and computer-readable media (CRM) for optimizing digital imaging. Although this section focuses on the drawings herein, and the specific embodiments found in those drawings, parts of this section may also have applicability to other embodiments not shown in the drawings. The limitations referenced in this section should not be used to limit the scope of the claims themselves.

The processing of data for the purposes optimizing digital images of propagation volumes described below may be performed using one or more processors distributed over various devices of an imaging system 100, i.e., a type of hardware and software infrastructure. Additionally, any processing and functionality of or relating to any aspects of any of the methods, systems or CRM herein can be implemented using conventional or special-purpose hardware, software, and/or firmware. Data handled via such processing or created resulting from such processing can be stored in any type of memory and/or readable media as is conventional in the art. By way of example, such data may be stored in a temporary memory, such as in the RAM of a given computer system or subsystem. In addition, or in the alternative, such data may be stored in longer term storage devices, such as magnetic disks, rewritable optical disks, and so on. For purposes of the disclosure herein, a computer-readable medium (CRM) may comprise any form of data storage mechanism, including existing memory technologies as well as hardware or circuit representations of such structures and of such data. Client devices, server devices, and network devices may include processors, memory, and storage devices, among other components.

The techniques used with the exemplary systems and methods may be implemented using a variety of technologies. For example, the systems and methods described herein may be implemented in software running on a programmable processor or may be implemented in hardware utilizing a combination of microprocessors and other specially designed applications, specific integrated circuits, programmable logic devices, or various combinations thereof. Also, the methods described herein may be implemented by a series of computer-executable instructions residing on a storage medium such as a carrier wave, disk drive, or other computer-readable media.

FIG. 1 is a schematic diagram of an imaging system 100 implemented on a network of client devices and server devices. The network of client devices and server devices may be interconnected. The computer hardware and system connectivity of FIG. 1 are illustrative and various other configurations of devices and components may be used to carry out some or all the methods disclosed herein for acquiring data relating to seismic surveys and generating optimized digital images based on the acquired data, e.g., as described in certain embodiments herein. The imaging system 100 may include any one or more of several client devices, server devices, and/or network devices. Client devices may include any device, e.g., personal computer, laptop, smart phone, tablet, thin-clients, or web-based appliance, capable of operating a web browser, displaying interfaces, and/or executing software instructions. Server devices may include any device, e.g., web server, application server, database server, or authentication server, capable of receiving and responding to requests made by client devices or other server devices. Network devices may include any device, e.g., firewall, hub, bridge, repeater, switch, or router, capable of transmitting requests and responses between devices on the imaging system 100. The network devices may be connected to various other networks, e.g., internet, intranet, or virtual private network.

The process of data collection, handling, and processing by the system 100 may be distributed among various devices that may be part of the imaging system 100. Executable instructions may be installed on each of the devices to receive, transfer, store, and/or process the data. Each device or set of devices may represent a logical layer through which data may flow and be processed.

FIG. 1 illustrates an exemplary set of logical layers 102-112 of the imaging system 100. In the client layer 102, client devices may display graphical user interfaces via web browsers or desktop applications, through which a user may input data, review data, and view the results of processed data. Web servers clustered in a web farm in the presentation layer 104 may receive and respond to requests originating from client devices running in the client layer 102. Also, the presentation layer 104 may be a first of various layers used to authenticate and validate user authority to access the imaging system 100. Application servers of the application layer 106 may receive data and requests originating from the presentation layer 104 and be instructed to process data, which may be returned to the presentation layer 104. Alternatively, the application layer 106 may receive data and requests originating directly from the client layer 104, i.e., from smart phones and devices running desktop applications. Additionally, the server devices of the application layer 106 may be instructed to send instructions to servers of the data storage layer 108 to store data, e.g., raw data and/or processed data, for later retrieval. Furthermore, server devices of the application layer 106 may be instructed to request data from other application layers 110 and 112, e.g., third-party platforms, intranet systems, and/or extra-network systems. Arrows in FIG. 1 depict paths of data flow between different layers of the imaging system 100. The arrows represent one or more network connections, e.g., as part of an internet, intranet, extranet, and/or virtual private network.

Although the imaging system 100 may be described as executing or performing steps or functions, those skilled in the art should understand that an individual or person is responsible for the action of the imaging system 100. For instance, a programmer may implement software which may instruct the imaging system 100 to automatically perform one or more steps or functions based on some input, e.g., from a person, another system, or clock.

Figure 2:
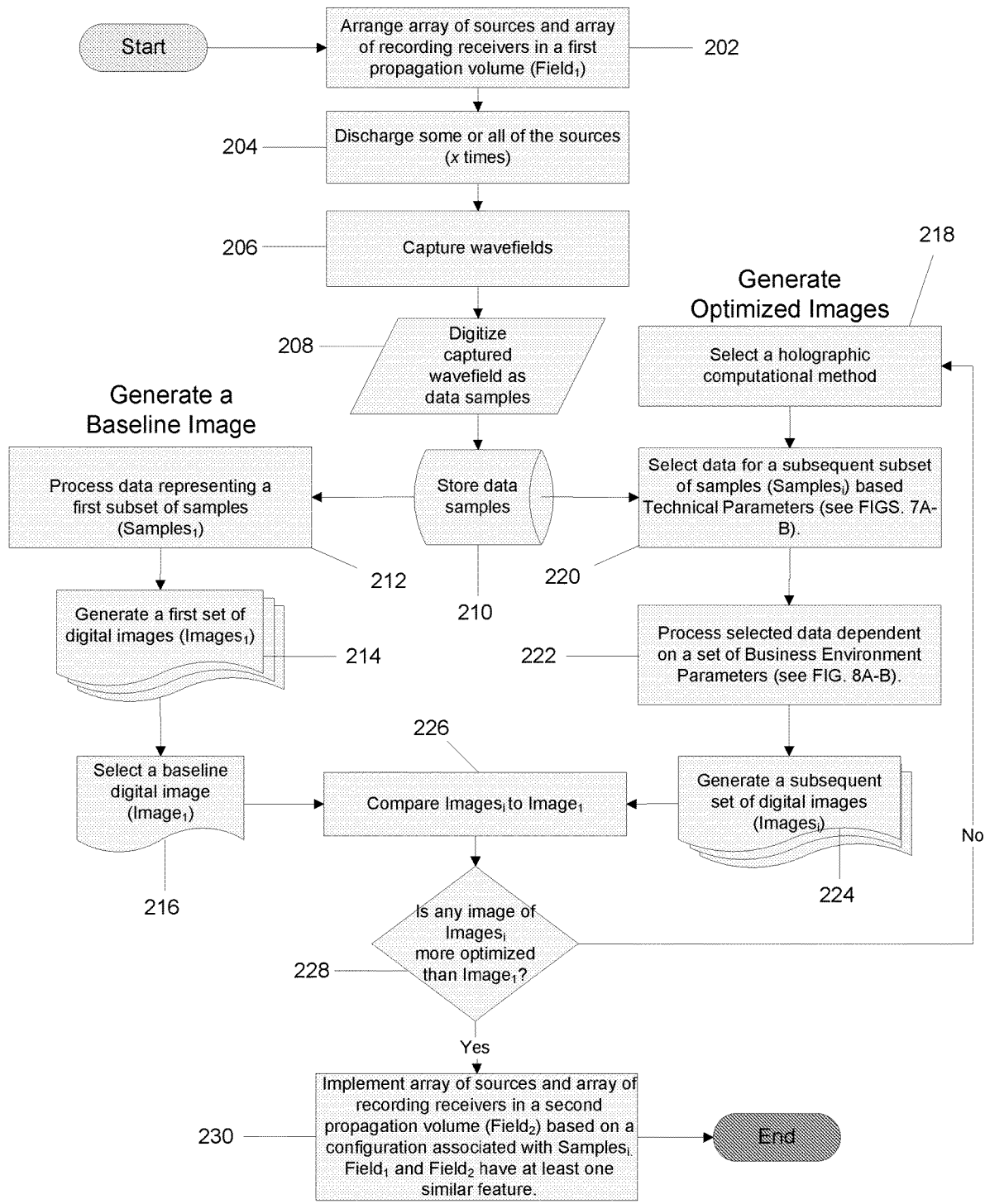
FIG. 2 illustrates general steps of a process for providing a digital image.

FIG. 2 illustrates a flowchart diagram of steps to optimizing digital imaging of propagation volumes, e.g., geophysical volumes. The steps may be grouped as: 1) capturing wavefields (exemplary steps 202-210), 2) generating and selecting a baseline digital image (exemplary steps 212-216), and 3) generating an optimized digital image (exemplary steps 218-228).

The group of steps for capturing wavefields may include: (a) step 202 for arranging an array of sources and an array of receivers in a first survey field ("Field1"), e.g., geophysical field; (b) step 204 for discharging, one or more times, some or all of the sources of the array of sources; (c) step 206 for capturing wavefields with the receivers of the array of receivers; (d) step 208 for digitizing captured wavefield as data samples; and (e) step 210 for storing the data samples.

Steps 212-216 for generating and selecting a baseline digital image may be performed by the imaging system 100. However, in some cases, steps 212-216 may be performed by one or more systems unrelated to and/or disconnected from the imaging system 100. In those cases, data samples of wavefield captures and baseline images resulting from those data samples may be acquired and copied to one or more databases of the system 100.

The group of steps for generating a baseline digital image include: (a) step 212 for processing data representing a first subset of samples ("Samples$_1$") from the data samples of step 208; (b) step 214 for generating a first set of digital images ("Images$_1$") based on Samples1; and (c) step 216 for selecting a baseline digital image ("Image$_1$") from the first set of digital images, Images$_1$.

Figure 7A:
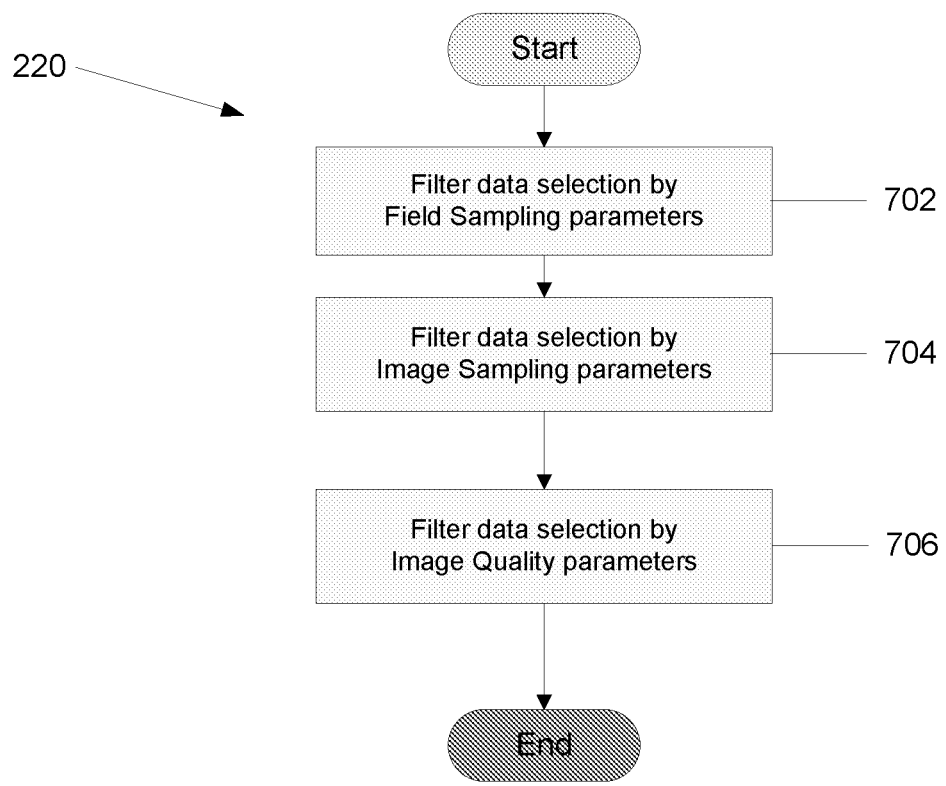
FIG. 7A illustrates steps for selecting data samples.
Figure 7B:
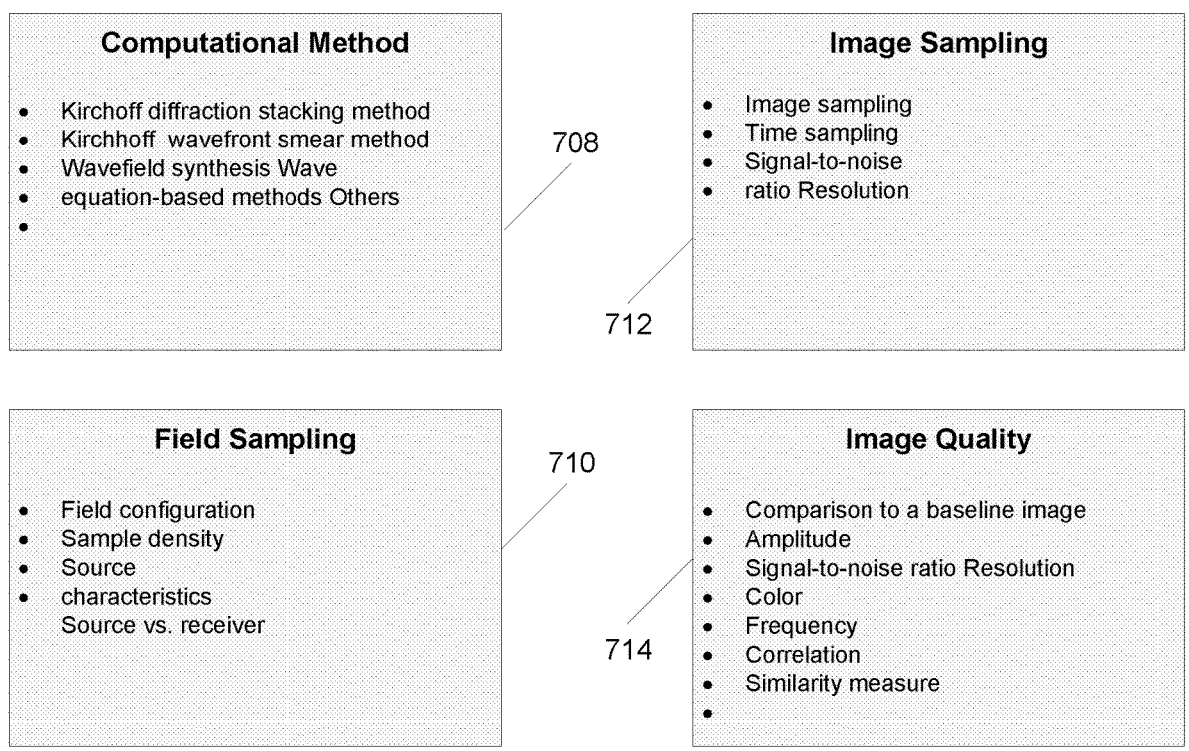
FIG. 7B illustrates technical parameters used to select and process data samples to generate a digital image.

The group of steps 218-228 for generating an optimized digital image may include: (a) step 218 for selecting a holographic computational method; (b) step 220 for selecting, from the data samples of step 208, data representing a subsequent subset of samples ("Samples$_i$") based on technical parameters (see FIG. 7B); (c) step 222 for processing the selected data dependent on a set of business environment parameters (see FIG. 8B); (d) step 224 for generating a subsequent set of digital images ("Images$_i$"); (e) step 226 for determining whether any image of Images$_i$ is more optimized than Images$_i$ and (f) step 228 for repeating steps 218-226 until an image of Images$_i$ has a value indicating greater optimization than Image1 or all holographic computational methods have been selected and executed.

If a new image of Images$_i$ is determined to be more optimized than Images$_1$, later seismic surveys at a second survey field ("Field$_2$") may be conducted in step 230 implementing an array of sources and an array of receivers in the second survey field based on one or more configurations associated with Samples$_i$ for subsequent digital images generated. Additionally, the later seismic surveys may also be conducted based on business environment parameters associated with Samples$_i$.

Capturing Wavefield Data

Figure 3:
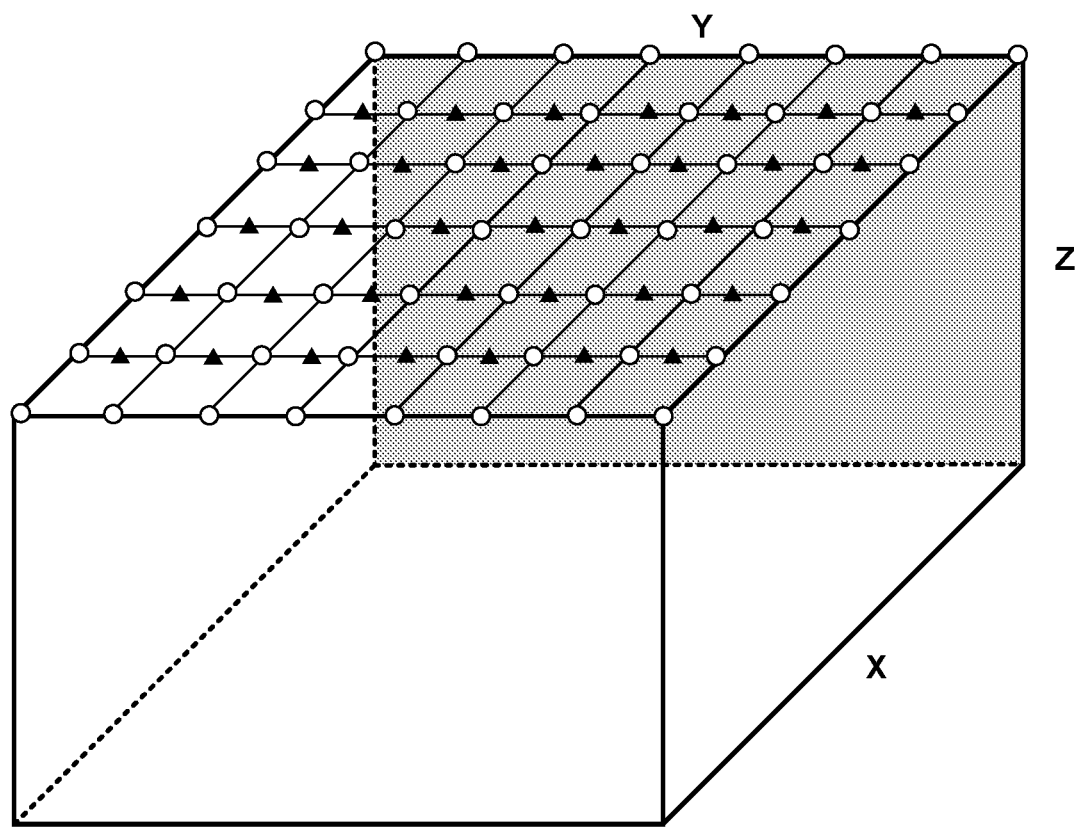
FIG. 3 illustrates an exemplary placement configuration of sources and receivers on a propagation volume for wavefield acquisition.

Referring to the group of steps 202-210 for capturing wavefields in a propagation volume in the flowchart of FIG. 2, field engineers may first arrange an array of sources and an array of receivers in a first survey field (Field$_1$) in step 202. An exemplary arrangement on the surface of a propagation volume, e.g., oil and gas field, described by Cartesian coordinates is shown in FIG. 3. A source is shown as a triangle. A receiver is shown as a circle.

In step 204, the field engineers may discharge, one or more times, some or all of the sources of the array of sources. Each discharging source may discharge energy, e.g., sound and/or light, into the propagation volume, away from source (see FIG. 5A). The discharged energy may propagate through the propagation volume. Various bodies, e.g., rocks, water, and hydrocarbon, may receive the energy. Each body may cause the propagating energy to be reflected and/or diffracted from the body. The reflected and/or diffracted energy may be propagated towards a receiver (see FIG. 5B). The discharged energy reflected and/or diffracted within the propagation volume, e.g., towards a receiver, may be referred to as a propagating wavefield.

In step 206, receivers in the array of receivers on the surface of the propagation volume may receive the propagating wavefield. Additionally, each receiver may record one or more characteristics of the propagating wavefields, e.g., acceleration, velocity, and/or direction, from each source that discharged.

In step 208, each receiver of the array of receivers may record one or more characteristics of the propagating wavefields, e.g., acceleration, velocity, and/or direction, that it receives by digitizing, e.g., converting energy signals from propagating wavefields, into digital data. The digital data may include information representing an identifier for the receiver, an identifier for the source, frequency of the energy received, and amplitude of the energy received.

In step 210, each receiver of the array of receivers may send the digitized data to a database server. The database server may assign a unique identifier representing the receiver, a source, the receiver, and one or more portions of the propagating wavefield received by the receiver.

The speed of travel for electromagnetic signals (like light or radar) in propagating wavefields requires sampling in nanoseconds or smaller time scales, which may generate large amounts of data in the magnitude of terabytes or larger. Because of computer technology limitations, previous imaging systems could only be implemented by analog methods, using coherent wavefield sources like lasers, and photographic recording. Hence, there may still some prevailing association of the term holography with optical methods. However, with the current digital imaging system 100 as illustrated in FIG. 1, digital methods may now be applied. Moreover, modern digital ground penetrating radar systems are a good example of such technology using electromagnetic wavefields. Current hardware and technology such as those implemented in the imaging system 100 may have the computational and storage capacity to process terabytes or more of data. Thus, in step 210 of FIG. 2, the digitized data may be stored on a database. The database may be part of the imaging system 100 or a on separate system accessible by the imaging system 100.

Wavefields of various types may be used for a variety of important applications. A wavefield may propagate in time within a Cartesian volume. Using digitized recordings in space and time of wavefields, digital images may be constructed based on data representing propagation volumes. An image volume then coincides with the propagation volume in whole or part. The propagating wavefield as recorded, may represent a "wavefield capture" or a "data capture," which may be discretely sampled in all dimensional variables (X, Y, Z and T). These recordings collectively may constitute yet a third volume, e.g., a data volume.

Generating or Acquiring a Baseline Image

Figure 5A:
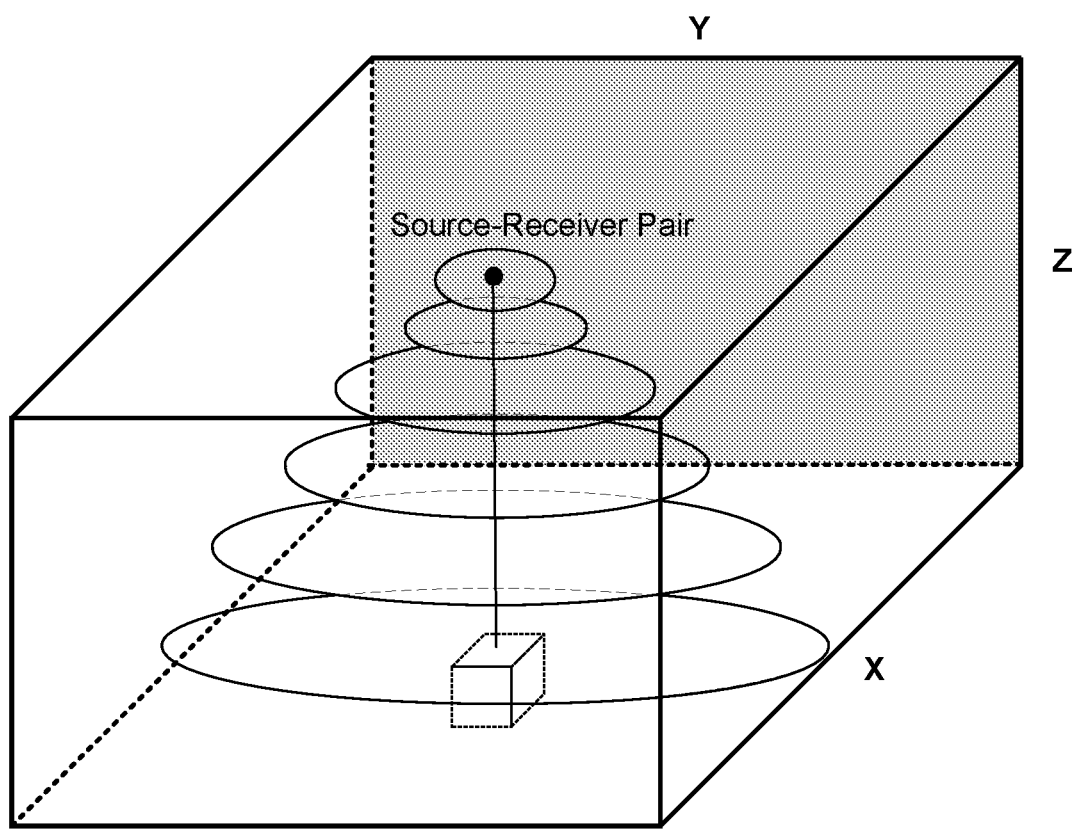
FIG. 5A illustrates a voxel in a propagation medium illuminated by a wavefield having a source directly above it.
Figure 5B:
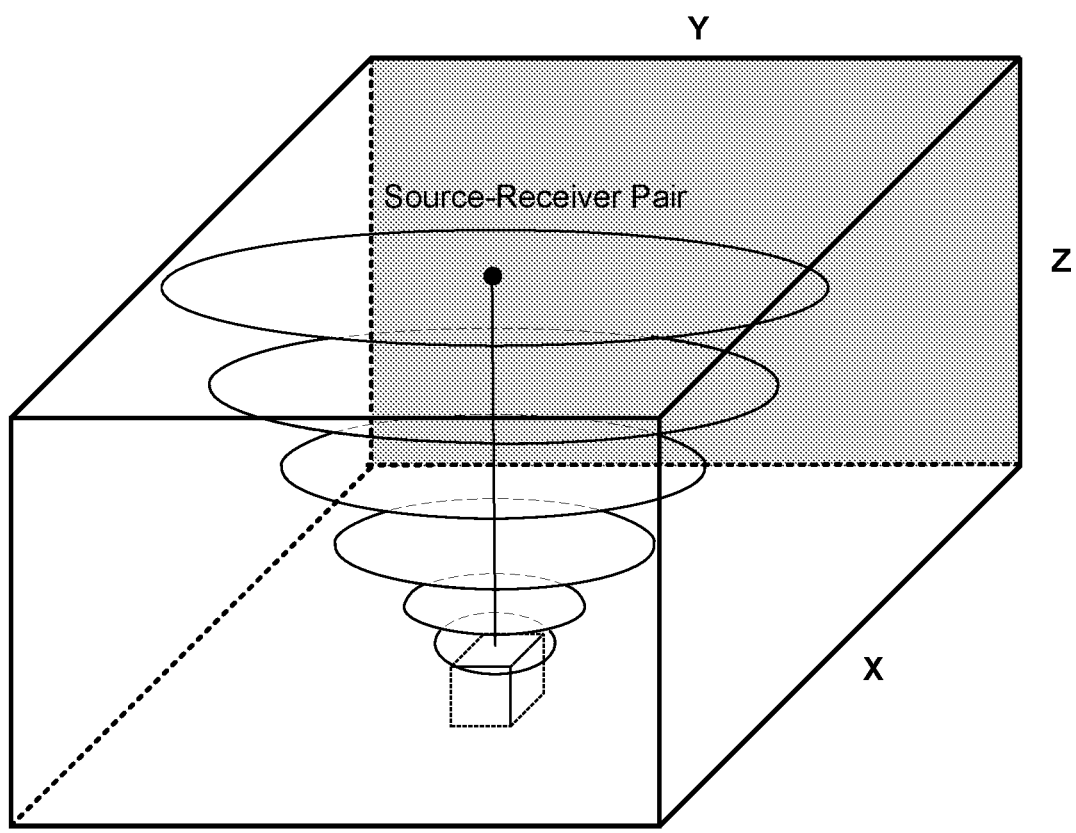
FIG. 5B illustrates the voxel in a propagation medium illuminated by a wavefield having a source directly above it showing the reflected wavefield from it.

The imaging system 100 may be capable of performing steps 212-216 for generating a baseline image. However, it should be understood that one or more separate systems, independent of the imaging system 100, could perform steps 212-216. Additionally, the step 214 of generating a baseline image using the stored data sample may be accomplished by any known method. Those methods may include, inter alia, the Kirchhoff diffraction stacking method (as shown in FIG. 5A and FIG. 5B), the Kirchhoff wavefront smear method, wavefield synthesis, and wave equation-based methods.

Regardless of how the digital baseline image is generated, the imaging system 100 may receive the digital baseline image, e.g., via electronic upload or digital scan. The imaging system 100 may store the digital baseline image in memory for later use.

Generating Optimized Digital Images Using Holographic Imaging

Referring to steps 218-228 for generating optimized digital images, what may be imaged from a volume depends on the wavefield and the application. At least three wavefield-related items can be imaged: 1) one or more active wavefield sources, 2) the propagating wavefield itself, and 3) the propagation medium representing the wavefield propagation volume. The wavefield propagation volume may also be described by Cartesian coordinates. Because the wavefield is recorded in time T, an image volume may also be scaled in time, then having coordinates X, Y, and T. Additionally, the image volume may be formed as well using the X, Y, and Z coordinates as desired.

A wavefield originates from one or more sources, and may be detected by one or more receivers, where recordings can be made. Each data sample of the wavefield capture may represent a scalar or vector quantity at a time (referred to a particular time reference) and may be related to coordinates describing location of each of the one or more sources and the one or more receivers. Typically, this may involve at least seven coordinates.

Although a data sampling for X, Y, Z, and/or T may be irregular or even randomized for one or more coordinates (whether by nature or by design), and also sparser, all concepts as explained or disclosed herein are described in terms of a sampling, e.g., regular sampling, for each coordinate. Data treatments for imaging with other sampling distributions, while introducing greater complexity, also may have some of the properties of methods as described herein.

For any data sample within the wavefield data capture associated with the Cartesian propagation volume (in X, Y, and Z coordinates), the data sample may be placed within a defined "volume." Doing so may provide for better organization of digital imaging computations. Because a recording has at least one identifiable source and receiver, that recorded signal or "trace" may be located vertically below the midpoint for that particular source-receiver pair as projected upward on to the propagation volume surface. Accordingly, a recorded data volume may be represented by coordinates X, Y, and T. Moreover, a time T at any particular sample from that trace may originate from responses from different voxels within the Cartesian propagation volume and also relate to different source-receiver pairings.

Figure 4A:
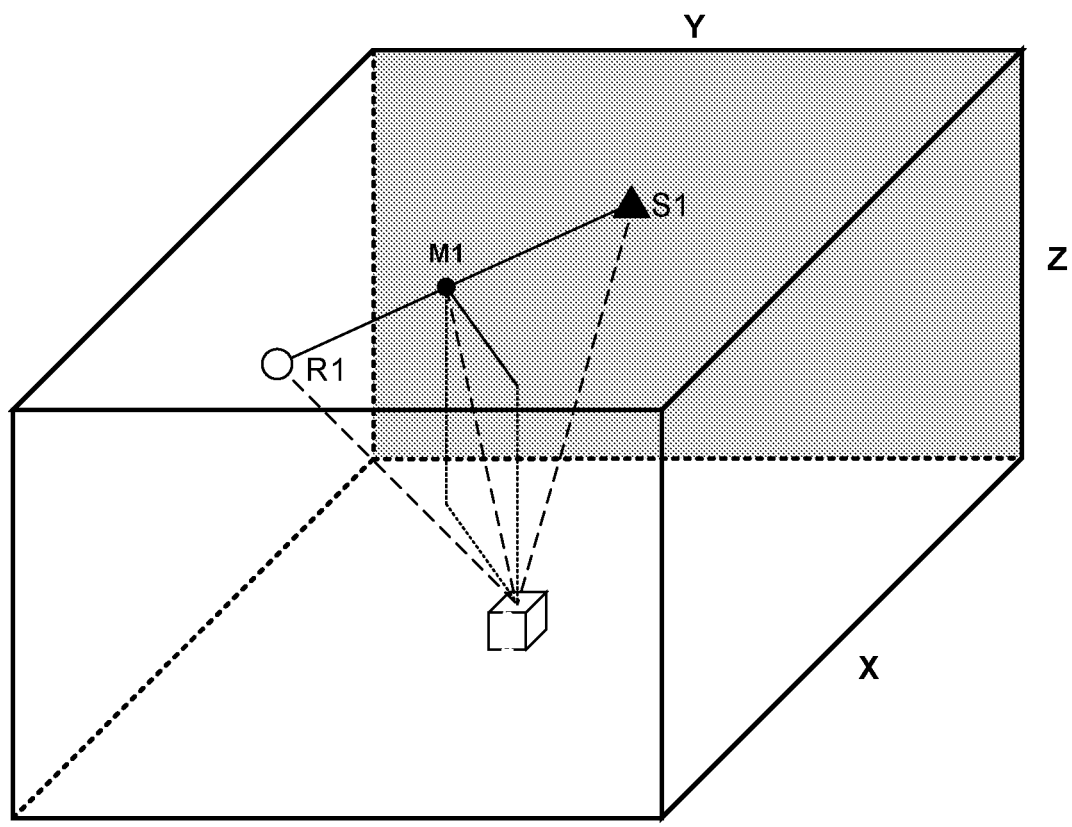
FIG. 4A illustrates voxel contributions for a source-receiver pair.
Figure 4B:
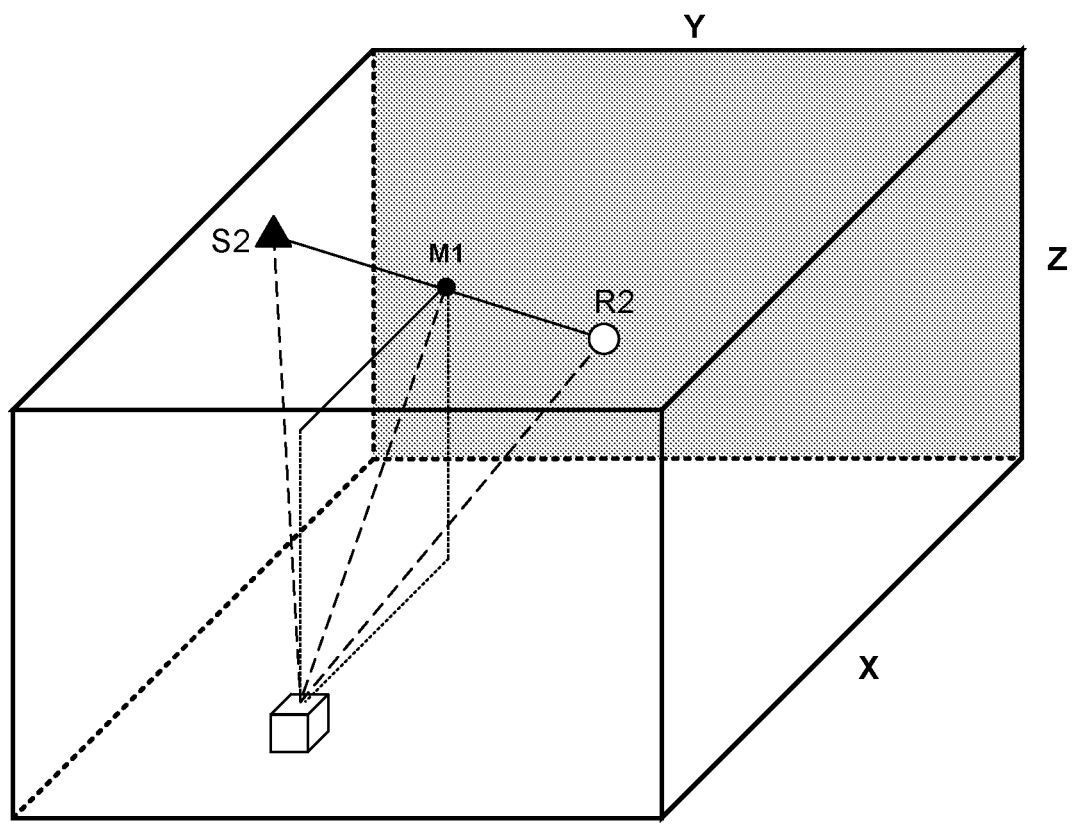
FIG. 4B illustrates voxel contributions for another source-receiver pair.
Figure 4C:
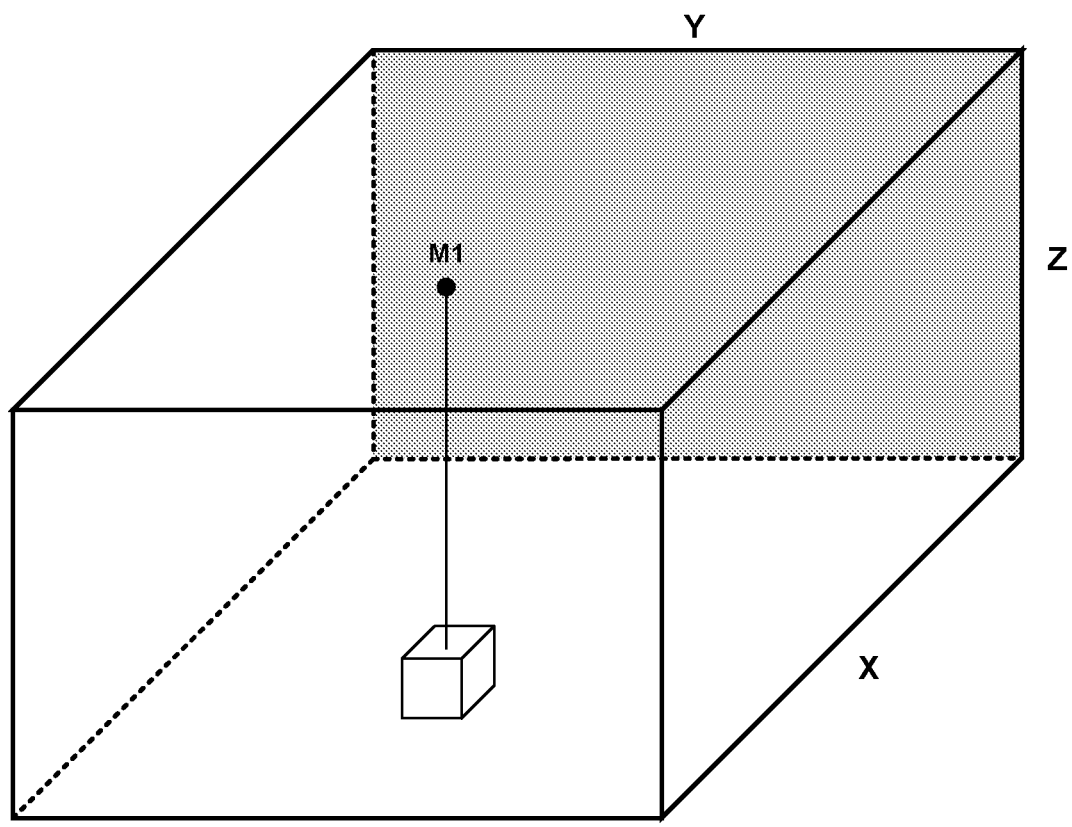
FIG. 4C illustrates a voxel in an image volume.

The views A-C of FIG. 4 illustrate the nature of a data volume from a wavefield capture. FIG. 4A illustrates a voxel contribution for source-receiver pair 1 positioned in a data capture volume below a midpoint location M1. FIG. 4B illustrates a different voxel contribution for source-receiver pair 2 but also having midpoint location M1 and arriving also at the same time as the source-receiver pair 1. The source-receiver midpoints on the surface for source-receiver pairing 1 and source-receiver pairing 2 may be coincident. FIG. 4C illustrates a voxel from the image volume also below position M1.

Different voxels in a propagation volume may have identical recorded travel times for two different source-receiver pairs. Those voxels may be positioned at the same location in the wavefield capture volume using midpoint positioning. Using midpoints to "locate" recordings may provide an effective means for organizing and handling the data capture and computing image volumes therefrom.

Hence, the voxels or data samples within a data volume or wavefield capture may either be viewed as 1) multi-valued or 2) a "family" of coincident volumes related to each active separate source (or equivalently each receiver for all sources). For each family member volume, there may in some cases, be no coincident recordings at midpoints. A voxel in the data capture volume below a midpoint at a particular time may represent contributions from many subsurface voxels within the propagation medium as shown. However, in the counterpart image volume voxel, for X, Y, and Z or T, there may be only a single value (see FIG. 4C). The imaging system 100 may use the data capture or data volume to form image volumes representing defined characteristics of or within the propagation volume, and more effectively according to one or more defined optimization criteria as will be discussed below.

Holography involves the encoding of some, or preferably all, wavefield information within a propagation volume. If a single voxel within a Cartesian propagation volume represents a point reflector or diffractor, acting according to Huygen's principle, like a new source, the voxel may spread an illuminating wavefield out in all directions. Accordingly, recorded contributions arising from that voxel within the full wavefield or data capture may be used to generate an image related to that voxel. That voxel may represent an elemental component of a body or some other physical structure.

Voxel information "encoding" within a recorded wavefield capture may be treated as holographic because of its physical nature. The voxel information may be used with digital methods of information recovery for imaging. FIG. 5A shows a diagram of such radiation encoding for a single featured voxel or point diffractor within a uniform propagation volume illuminated from directly above it. The geometry of the wavefield signature for a spike-like source has the form of an expanding spherical downward traveling wavefield which on encountering the featured voxel, reflects another expanding spherical wavefield (see FIG. 5B), part of which travels upward to the surface of the volume where it may be recorded. This behavior is precisely as described by Huygen's Principle.

Figure 5C:
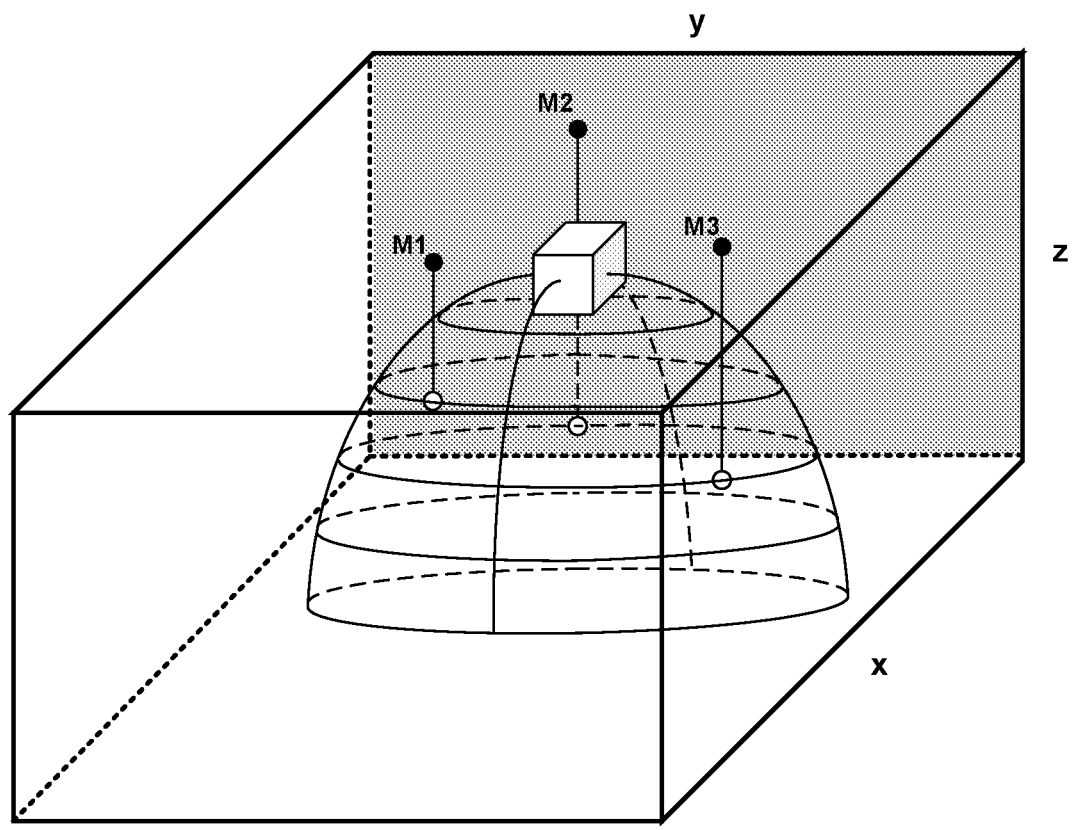
FIG. 5C illustrates a hyperboloid of revolution surface representing a common source-receiver separation and three exemplary intersecting recorded traces, M1, M2, and M3.

To recover an image of the voxel from the recorded wavefield, all surface recordings for such information in the data capture or data volume may be analyzed. FIG. 5C illustrates imaging for a subsurface voxel of FIGS. 5A-B using a hyperboloid of revolution imaging surface in the data volume for a common source-receiver separation by summing the recorded wavefield values from trace intersections with this surface. The hyperboloid surfaces may be different for each constant source-receiver separation and become "flatter" as the separation increases.

Three recording locations represented by their midpoints (M1, M2, and M3) are shown in FIG. 5C, as vertical traces that intercept the wavefield hyperboloid of revolution imaging surface at different points. Summing the recorded wavefield values at those intersection points into the hyperboloid apex location forms the image voxel. The more intersections, the better the image.

Hence, following one method of wavefield data capture, recorded information from everywhere on this surface may be gathered from within the data capture to image a particular voxel, e.g., "parent" or featured voxel, from the propagation volume. Accordingly, recorded information may be gathered for all surface receiver recordings for each source, summing such information from interceptions with the appropriate hyperboloid surfaces as estimated, into the apex for each parent voxel as a simple means of forming its image.

Thus, each image voxel, in turn, would be treated as the featured voxel in the propagation volume, and for each surface midpoint location of the data capture, different imaging surfaces must be used for the different members of the data capture, as related to the source and receiver separations. This method results in summing great numbers of samples containing information from a parent voxel back into that voxel as a part of developing a full image volume voxel by voxel.

Another aspect of this the methods herein is to recognize that the properties of a real-world application for forming images from a recorded wavefield capture which has been discretely sampled, encompasses by its nature limitations and particular requirements. Those limitations and requirements may impact both the economics and efficiency of a data acquisition or capture, as well as the attainable resolution and quality of the final optimized image. The following discussion describes the processes from data capture through to imaging of propagation volume, providing optimal results via field practices, processing, computational algorithms, improved data and interpretive displays.

Every data sample or voxel of a wavefield capture represents one or more values, and has at least one source position, a receiver position, and a time as measured from a common reference. For purposes of data handling and analysis, voxel positions may be assigned in the data volume so a recorded data sample may be located within the data volume at a voxel location directly below an associated source-receiver midpoint, following the midpoint convention (see FIGS. 4A-B). The data sample may be used to 1) identify sources (as in stars for astronomy, or micro-seismic emissions as from subsurface rock fracturing positions), 2) the propagating wavefield (as in radar and sonar systems), and/or 3) the propagation medium itself (as sometimes sought in non-destructive testing, medical imaging, and exploration seismology).

As discussed, an image space or image volume may be coincident in whole or part with both a propagation volume and a data capture or a data volume. Returning to steps 218-228 of FIG. 202, image volumes may be formed within the propagation volume using the data capture volume according to analytic formalisms of processing data to generate optimized digital images. Steps 218-228 may provide input data samplings and imaging computations. Both field data sampling and discrete image sampling may be used in establishing comparisons between a baseline image and an optimized image.

In step 218, the imaging system 100 may retrieve a set of rules or parameters applicable to a type of holographic computational method. The holographic computational method may be from a group including, inter alia, the Kirchhoff diffraction stacking method, the Kirchhoff wavefront smear method, wavefield synthesis, and wave equation-based methods. The selected holographic computational method may be selected by a system operator or pre-configured in the imaging system 100.

Regarding step 218, there are many alternate methods by which the data capture or volume may be transformed into an image volume. It is very instructive however, to use some of the more common imaging approaches, using simplified scenarios, as vehicles to illustrate subtle elements arising from the discrete nature of the entire process. FIG. 4 shows how a single voxel, for the illumination by a single source, imparts its presence into the collective wavefield. This encoding of information is holographic as discussed above. For purposes of imaging that same voxel, the system 100 may assess the voxel's character from data from the recorded wavefield using the Kirchhoff diffraction stacking method or the Kirchhoff wavefront smear method. Both methods were developed by Gustav Kirchhoff (see Seismic Data Processing, Lecture 15, 2014).

Concerning a voxel of interest in a uniform propagation volume, as shown in FIGS. 5A-B, the effect of that voxel in the data capture is described by a surface in the form of a hyperboloid of revolution (for the constant velocities) in FIG. 5C. Imaging may be performed by gathering the voxel expressions in the wavefield using the surface as shown FIG. 5C, and its interceptions with the vertically plotted recorded data within the data capture. Similar operations may be done for every voxel, and for every source-receiver separation. For every source, the data samples addressed in generating the image are at a greater depth (or time) than the voxel of interest. This method of imaging may be known as the Kirchhoff diffraction stack method in seismic exploration imaging.

Figure 6:
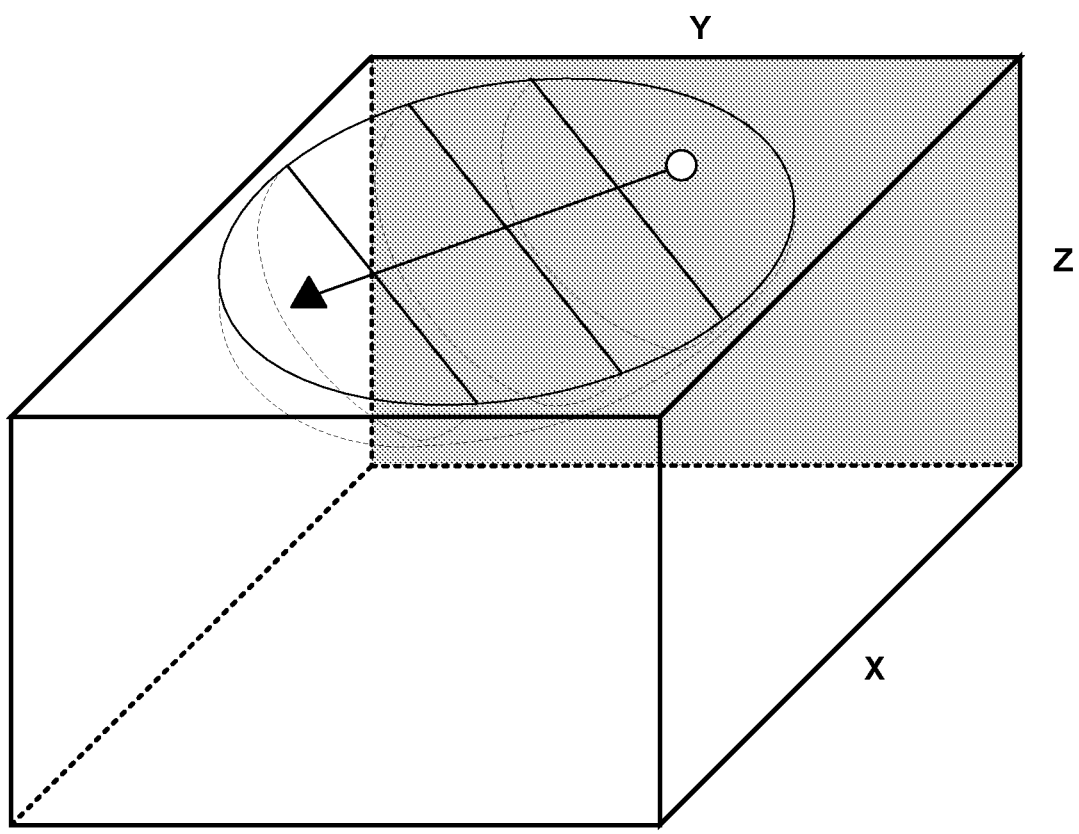
FIG. 6 illustrates a half ellipsoid of revolution surface formed in an image volume.

Alternatively, the Kirchhoff wavefront smear method may also be used to generate a digital image of a propagation volume. Referring to FIG. 6, drawing again on the data volume for a particular source, the travel time at the receiver shown (for a constant velocity) may have derived from any point on the half ellipsoid of revolution surface. Summing the recorded value for the travel time into every image voxel which intercepts the ellipsoidal surface of revolution related to that time, may enhance and recover the individual voxel signatures, and again form images. The wavefront smear method may distribute information only to samples above the sample of greatest depth (or earlier in time) on any such imaging surface.

Similar procedures in other particular imaging applications, have other names or descriptors like "Synthetic Aperture" exploit analogous ideas of information enhancement. There is also a prevailing perception that all such methods, e.g., Kirchhoff diffraction stacking method and Kirchhoff wavefront smear method, are essentially equivalent in their imaging performance. However, for discrete wavefield samplings these notions are not correct. To attain better sampling at the greatest recorded depths or recorded times, the Kirchhoff diffraction stacking method should not be used alone. Conversely, the Kirchhoff wavefront smear method would perform poorly for the earliest recording times or shallowest depths. These observations exemplify some of the special requirements stemming from the nature of discretely sampled Wavefield data, as considered here.

In step 220, the imaging system 100 may select from the database data for a subsequent subset of samples ("Samples$_i$") based on technical parameters. The technical parameters may be categorized as field sampling parameters (710, FIG. 7B), image sampling parameters (712, FIG. 7B), and image quality parameters (714, FIG. 7B). The imaging system 100 may filter the data selection for Samples$_i$ by field sampling parameters (702, FIG. 7A), image sampling parameters (704, FIG. 7A), and image quality parameters (706, FIG. 7A).

Image quality ("IQ") may represent one or more qualities or characteristics common between two images, e.g., a baseline digital image and a subsequent digital image, for comparison. An image quality parameter value may represent amplitude, signal-to-noise ratio, resolution, color, frequency, or correlation. For example, IQ measures may be based on likeness to a baseline digital image. IQ may be a measure in determining imaging effectiveness, and even acceptability. Thus, IQ may be a key component of optimization.

Once the imaging system 100 receives instructions to image a portion of a propagation volume, the imaging system 100 may assess associated data samples and image samples. It should be understood that there may be more data samples than image samples. Thus, a ratio M of data samples to image samples may be greater than 1—and, preferably the bigger M is the better.

The significance of IQ and ratio M may be illustrated in how an intended imaging procedure will draw upon all the parameters of consequence (see FIG. 7B and FIG. 8B), e.g., technical parameters and business environment parameters. Referring to FIG. 2, considerations for IQ and the ratio M may be applied to steps 218-228.

Consider a data volume stored in a database (from step 210). The data volume may represent all wavefield sources and receivers on an upper propagation volume surface. Assuming that all wavefield sources and receivers occupy proximate, regular positions (FIG. 3), the sources and receivers may each occupy a 10 sample by 10 sample rectangular grid. Such a scenario is shown in FIG. 3, with the two sampling grids on the propagation volume surface shown as being nearly coincident.

Also, assuming each recorded signal may be taken to include 100 time samples, each source, when discharged, would produce 100 recordings. There may be 100 sources, and each recording taken to have 100 samples. In all, 1 million data points would be acquired for the data capture in step 210. A standard convention (which follows principally from signal processing) for sampling the image volume from a wavefield capture may be used to "mirror" the acquisition parameters for that volume. Following this convention would lead to having an image volume representing a 10 sample by 10 sample surface grid, and 100 time samples. Hence, a resulting digital image may consist of only 10,000 samples, giving a value of the ratio M=100.

Because implementing sources and receivers on survey fields usually involve cost and effort, it may be obvious to ask whether a smaller value for ratio M (and hence a cheaper and faster acquisition or survey) could still produce an acceptable image. Indeed, there is another option under the holographic view. Suppose the imaging system 100 samples the image volume of the previous discussion with a 20 by 20 grid and use 400 samples over the same recorded time interval. This now gives 160,000 image samples, having a value of ratio M=6.25. Accordingly, the imaging system 100 may generate a subsequent digital image having far greater resolution in both the spatial and time coordinates than the image as first described, but the signal to noise ratio may be reduced.

Figure 8A:
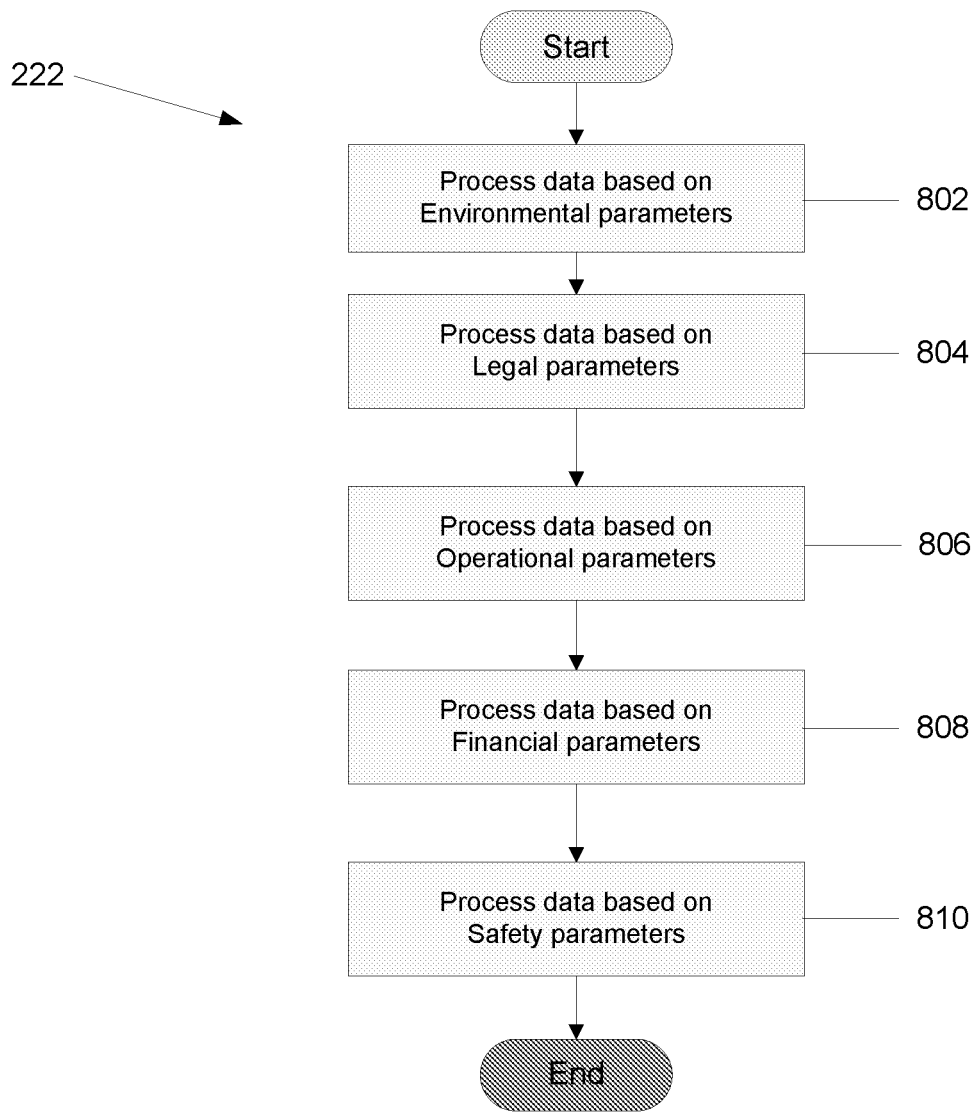
FIG. 8A illustrates steps for processing data samples into a digital image.
Figure 8B:
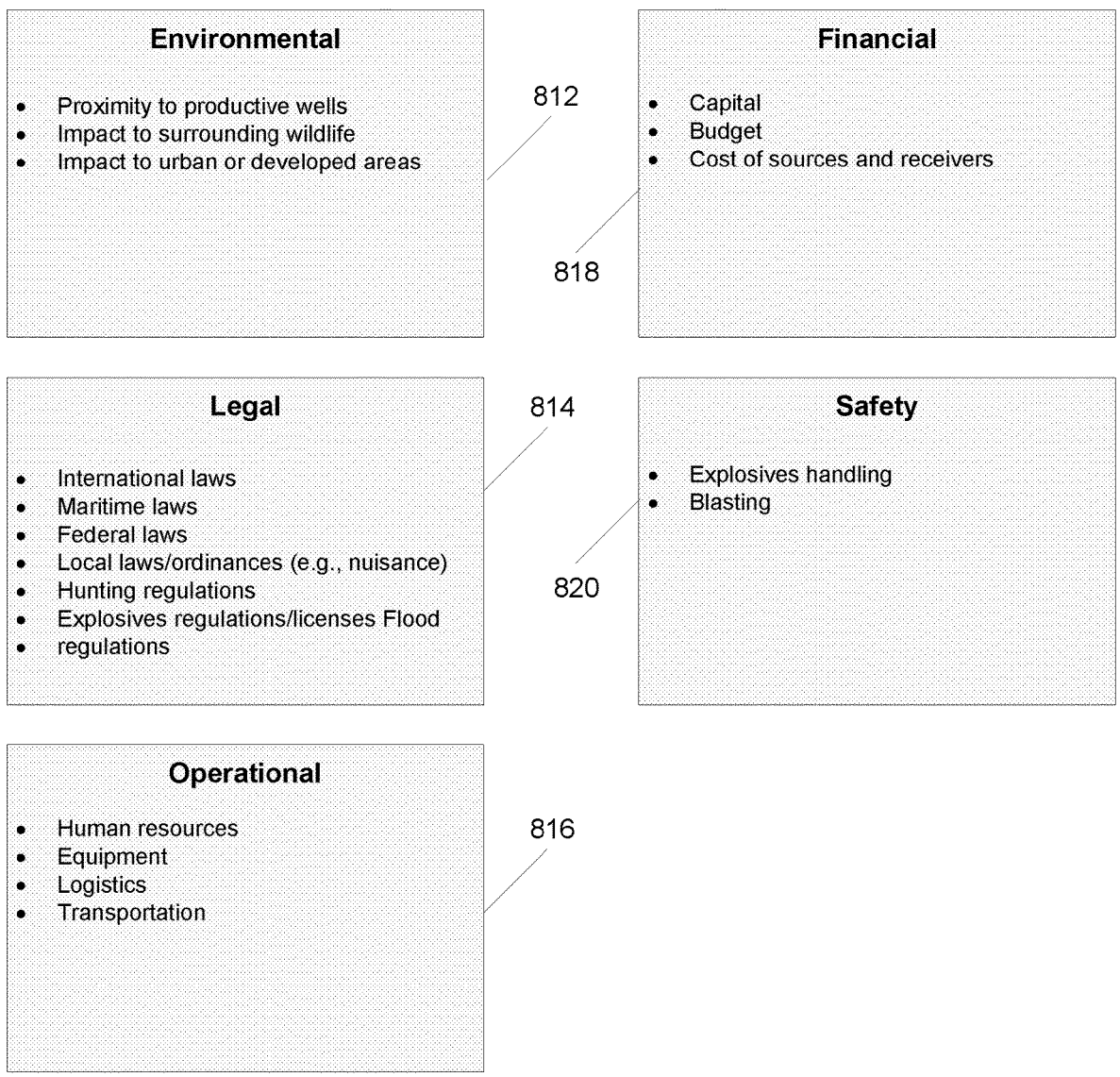
FIG. 8B illustrates business environment parameters by category used to process data samples to generate a digital image.

In step 222, the imaging system 100 may process the data for Samples$_i$ using business environment parameters (see FIG. 8A). Business environment parameters may include environmental parameters 812, legal parameters 814, operational parameters 816, financial parameters 818, and safety parameters 820 (see FIG. 8B). The business environment parameters may have competing considerations. For example, there may be consideration for lower costs and faster acquisition. Furthermore, there may be parameters requiring better images with even higher resolution. Thus, the imaging system 100 may be configured to use IQ and assess real-world business environment considerations for step 222, as well as for portions of steps 218-228 in FIG. 2.

As discussed above, alternative activities and considerations in digital imaging may affect real-world operational speeds, efforts, and costs. Likewise, those activities and considerations also may have consequences on generating subsequent digital images from Sample, in step 224. Accordingly, the imaging system 100 may process data with consideration for business rules and/or parameters. For example, consideration may be made for marine sound limits respecting certain marine life, medical energy radiation limits (as for X-rays and proximity to Radars), acceptable distances of energy sources from producing oil or gas wells, "no-go" areas such as missile testing zones or particular conservation habitats. Marine seismic source volumes are restricted so as not to harm marine life. Sound source levels for medical imaging must meet intensity standards to avoid tissue damage. X-ray radiation must meet analogous standards. Onshore seismic sources may not be discharged too close to a productive well to eliminate the possibility of formation damage. Some sound sources may not be used at all in environmentally sensitive areas. Particular survey methods have only limited application in urban and developed locations.

All such operational impediments and more must be honored by any lawful optimization procedure. Hence it is important to organize and acknowledge these business environment factors, e.g., parameters, more explicitly.

In step 226, the system 100 may compare a subsequent digital image with the baseline digital image. The baseline digital image may be considered to have acceptable IQ, because the baseline digital image is generated by current standard procedures, as applied to the data capture. However, concerning image comparisons and treatments, the differences between a baseline image and an optimized image may be significant, for example, when considering changes in underlying image resolution.

Consider two images of the same volume, using different samplings from the same data capture, both images having 100,000 samples. On inspection by the imaging system 100, one of those images may be identified as the reference standard. One reasonable likeness measure would be a volumetric normalized cross-correlation. A value less than one (1) may suggest that one volume of lower correlation value may not be as good; however, in some cases, which volume may not be known. Accordingly, some criterion must be used to identity the appropriate volume. Another factor, which can be justified by physical arguments, may be that the better image volume should be more energetic or brighter. Thus, the image having a greater sum of squares may be determined as being improved. Such comparative procedures may be implemented in step 226.

Suppose now one image has 100,000 samples while another starting from the same volume has 800,000 samples (step 216 versus 224, FIG. 2,). How should they now be compared, to determine some measure of IQ? The image volumes are the same physical size, and the larger number of samples perhaps indicates better resolution (smaller voxels), but for a given data capture, sampling resolution improves only at the expense of decreasing signal-to-noise (SNR) content—often having lower values of the ratio M. The imaging system 100 may be configured to have one or more rules to accept the image having fewer samples as more reliable, but for an application requiring better resolution, the trade-off for lower SNR may be preferable. IQ measures in this case might include frequency and wave number criteria which recognize the bandwidth and wave number extension characteristics of greater resolution. For instance, imaging system 100 may be configured to have one or more rules to identify the digital image having the broadest spatial and time frequency bandwidths as better, according to percentage increases related to bandwidth extensions. Such approach would also include some noise threshold measure to unambiguously define bandwidth terminations.

Colors may be related to numerical values. The imaging system 100 may be configured to have one or more rules to compare and identify an optimized digital image related to those color values. If the color values are related to physical properties as opposed to esthetic criteria, there could be better color choices for producing particularly effective interpretive color displays.

In step 228, the imaging system 100 may determine whether the subsequent digital image has one or more characteristics identifying that the subsequent digital image is an improvement over the baseline digital image. If a characteristic is identified improved for the subsequent digital image, the system 100 may identify the subsequent digital image as optimized. If the subsequent digital image has no improved characteristic over the baseline digital image, then the imaging system 100 may repeat steps 218-228 until a subsequent digital image is identified as an optimized digital image or until all holographic computational methods have been executed.

Data Presentations, Interpretive Concerns, and Illustrations

Application of steps 218-228 for generating optimized digital images of wavefield data may decrease costs and effort while improving quality of digital images of subsequent surveys of propagation volumes. The essential activity of presenting wavefield imaging results for their intended use may be called "interpretation." In step 230, interpretation of the digital imaging process resulting in the optimized digital image may be applied to a future propagation volume. By applying one or more digital imaging parameters for the optimized digital image to survey activities for the future propagation volume, operators may realize lower costs and more efficient source-receiver array designs, among other improvements related to business environment parameters.

While for some applications, computations using the image can provide information as is sought, for others, machine learning or Artificial Intelligence (AI) may provide the desired answers. Many applications, however, will nevertheless require human insights and judgements, to determine or estimate requisite intelligence from an image. For all cases, the measures ratio M and IQ as previously introduced play important roles, yet there are also other dimensions of importance. One such dimension recognize may be introduction of quantitative measures within the image, where possible (step 228, FIG. 2). Such characteristics can frequently offer advantages.

When quantitative measures can be related to absolute references, even in approximation, such information can be significantly more valuable than simple empirical comparisons of likeness or magnitudes. This axiom follows from the fact that all applications of interest involving wavefields are related to physical processes and real materials. A good and quite common example for many wavefield applications would consider estimating propagation velocities within the Cartesian volume. Recognizing differences in velocity and even having some sense of magnitudes of differences might be beneficial, of course, but knowing estimates of actual velocities often can identify particular materials and sometimes even provide vital interpretive insights. For example, how much faster or slower would sound travel in healthy tissue in contrast to different tumors?

For applications in exploration seismology for finding oil and gas or defining hydrocarbon reservoirs, quantitative velocity estimates can provide information concerning hydrocarbon presence (and often distinguish between gas and oil), porosity developments, presence of rock fracture "swarms", and when used in conjunction with observed geometries, still additional information related to important physical properties. Similarly, we might ask, would imaging a far-off aircraft in detail using radar, be more advantageous than just detecting a "blip"?

While the concepts within this disclosure have been framed in very general terms, it would be instructive to show concrete examples, where most of the principles discussed, and the steps of FIG. 2 are employed in varying ways, offering some variety of illustrations. Since any specific applications could involve much matter extraneous to the importance of the imaging results, minimal discussion in this regard is included here, but references providing greater detail are identified.

Figure 9:
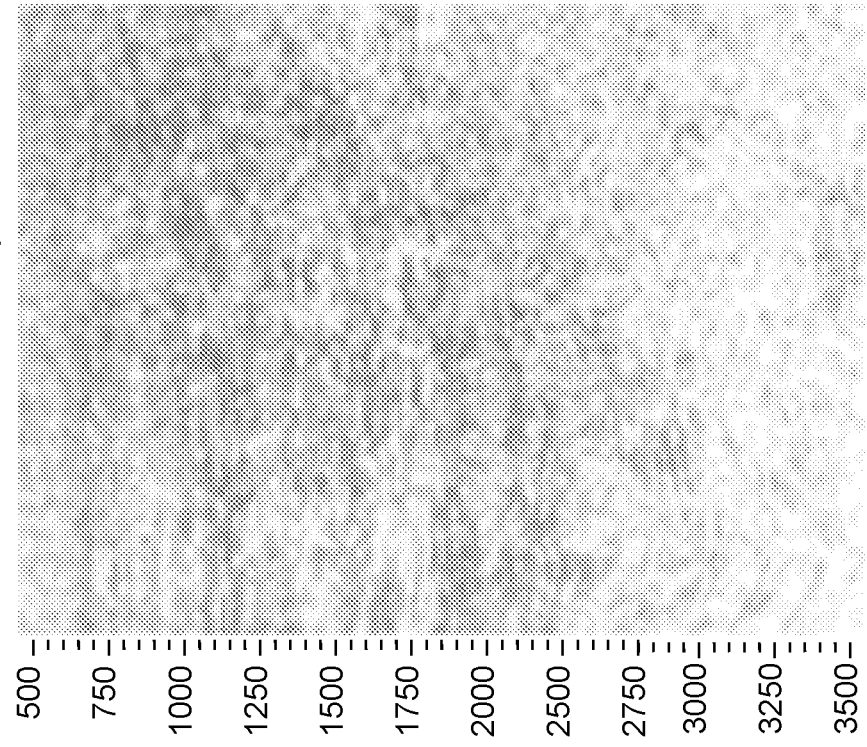
FIG. 9 illustrates images of a reflection wavefield from the transition zone subsurface survey undertaken along the Louisiana coastal transition zone.
Figure 9:
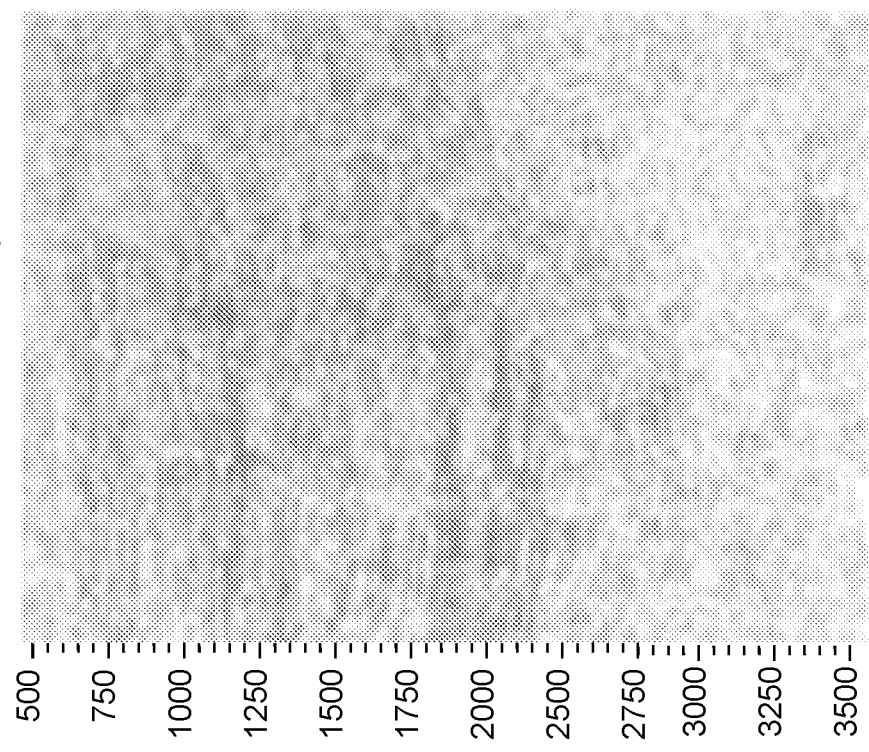

The following seismic exploration examples in FIGS. 9-13 may be considered because their field implementations look much like the wavefield acquisition models as shown in FIG. 3. FIG. 9 illustrates images of a reflection wavefield from the transition zone subsurface survey undertaken along the Louisiana coastal transition zone just to the east of the Texas state line. A grid of sources and receivers were deployed much like FIG. 3. The sources and receivers covered a 5-mile by 25-mile strip bracketing the boundary from a portion of the Texas coast into to the waters of Gulf of Mexico. Recordings were arranged so that one vertical image trace would be produced every 55 ft in each direction over the propagation volume, with 1250, four msec time samples recorded for each recorded trace. Projected cost was bid at $25,000,000.

The survey data represented a reflection wavefield from the transition zone subsurface, using conventional procedures to form an image volume using step 216 in FIG. 2. However, in planning for this survey, a previously existing nearby 3D propagation volume (step 212, FIG. 2), but entirely onshore, was also considered because it had acquisition parameters similar to the originally planned transition zone survey. Standard Imaging procedures had been applied to the existing survey using step 214. The image IQ for this volume was considered to be a quite good standard, and a representative Profile is shown in FIG. 9. The acquisition cost of this onshore survey had been $65,000 per sq mi.

The data capture (step 210, FIG. 2) from this onshore survey was then decimated to simulate removing every other Receiver line perpendicular to an equivalent "coastline", and also removing three out of every four Source positions. The result was equivalent to acquisition of traces having 220 ft×220 ft spacing—and representing ⅛ of the original data. Projected acquisition cost was estimated now to have been $45,000 per sq mi. The Imaging as formed from the decimated survey (step 222, FIG. 2), used a denser sampling to match that of the original undecimated imaging (see discussion of denser image sampling related to FIG. 9). The counterpart profile for such imaging is also shown in FIG. 9. From such testing it was also determined that a volumetric cross-correlation with the standard volume of 0.85 (a perfect match would be 1.00) would also be acceptable for the intended interpretations and other uses of the imaged data.

The transition zone survey as described was undertaken in practice but using the analogously decimated field practice. Image formation used a sampling as if from the originally planned undecimated survey. The Louisiana transition zone survey and imaging as described yielded excellent results. The resulting image had an acceptable IQ. It should be understood that a transition zone survey was considerably more complex and costly than a survey entirely on land. Proposed cost of the survey as originally planned was $25,000,000. The cost saving realized was $11,000,000 representing about 44% of the initially quoted figure. This work was reported in conjunction with Rudy Prince, at the 1998 Offshore Technology Conference (Neidell & Prince, OTC Paper No. 8678, 1998).

This simple test as presented clearly indicates that further examination and better organization of the ideas and data can be very worthwhile. There are other widely used seismic data acquisition methods, where similar ideas and procedures could have even greater economic impact. Marine surveys where receivers are placed on the sea bottom and using surface-towed Marine sources are very costly, but principally owing to receiver deployment involving placement on the sea-bottom. A ratio M relating to data acquisition and imaging samples may be held constant by increasing inexpensive source positions but using a less densely populated and less expensive receiver grid. Such a procedure may offer significant cost savings, as well as faster operations. The ratio M may be further reduced and still produce acceptable image IQ's with even added gains in image resolution. There are a number of other practical issues in the acquisition and in the image processing which may yet introduce additional constraints regarding interchange of sources and receivers. So, how could we know what best to do? The systematic testing inherent in the procedure of FIG. 2 is clearly necessary.

Figure 10:
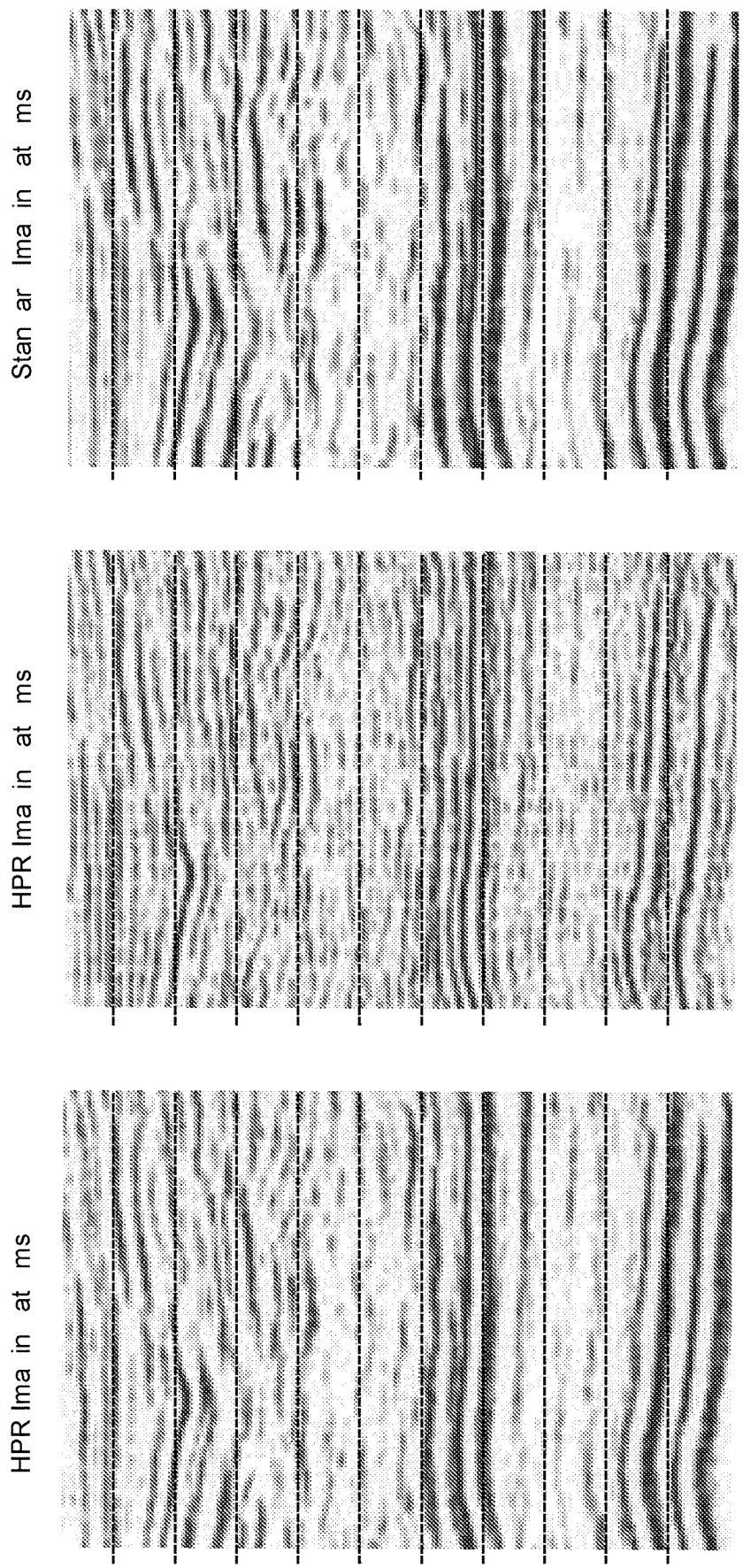
FIG. 10 illustrates images of a propagating wavefield sampled at different spatial and time intervals.

Note now a single profile from a 3D onshore seismic survey as processed conventionally and displayed at the right-hand panel of FIG. 10 in the conventionally used imaging format. The display for the rightmost panel having ratio M as a reference value was deemed to be of acceptable IQ for interpretation. It shows the propagating Wavefield sampled spatially at 110 ft spatial intervals with 2 msec time samples. At the far left, the spatial resolution is doubled by spatial sampling now at 55 ft intervals. Now we have ratio M/2, and we observe that spatial continuities are clearly improved. Any method of evaluation including spatial bandwidth measures would indicate improvement. Image pixel magnitude measures however would see lower amplitudes, and increased population of smaller values, indicating lowered signal-to-noise contributions. The center panel also shows 55 ft spatial sampling, but also with 1 msec time samples (for ratio M/4 now). Only the central panel shows the two discordant "flat" reflector segments (marked) which frequently are a most important indicator of hydrocarbon presence. How important then should resolution be as a factor for estimating IQ? Interpretation of medical images would clearly embody similar requirements.

Early lessons as just presented demonstrate that even for conventional seismic imaging, much of the implicit detail and information may not be readily perceived, owing to the inadequacy of the data displays. Surprisingly, such displays presently still dominate in the oil and Gas Industry and are widely used.

Figure 11:
FIG. 11 illustrates images of a seismic survey of a portion of the Texas Glenrose Reef using inversion information and display formats including an Extended Visual Dynamic Range color display format.
Figure 11:
Figure 12:
FIG. 12 illustrates images of a seismic survey of a portion of the Austin Chalk using inversion information and display formats including an Extended Visual Dynamic Range color display format.
Figure 12:
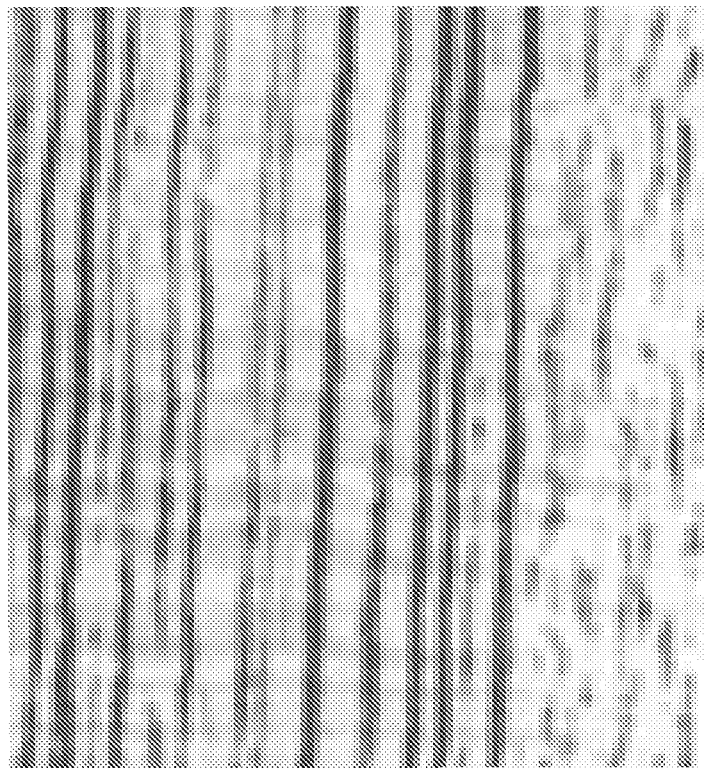

FIG. 11 shows a Glenrose Reef discovery in Houston County, Texas made starting from conventional seismic data processing in 1985. The underlying data capture was a 2D grid of profiles. Empirical methods were used to scale the seismic data quantitatively as Velocities (referred to as an "Inversion"), but with an extended visual dynamic range (EVDR) color display format applied. We shall comment further on this procedure shortly. The contrast in information content is most evident. The Glenrose Reef (the Eastham State Prison Farm Field in Houston County, Texas) still produces oil today, 30 years after its discovery. Similarly, an analogous Austin Chalk discovery made in the 1990's is shown in FIG. 12. Here the hydrocarbon filled porosity zones show themselves also as contrasting velocity drops (in orange) within the light blue Middle Chalk member. Such imaging may be ideal today for planning and guiding the drilling of horizontal wells.

Figure 13:
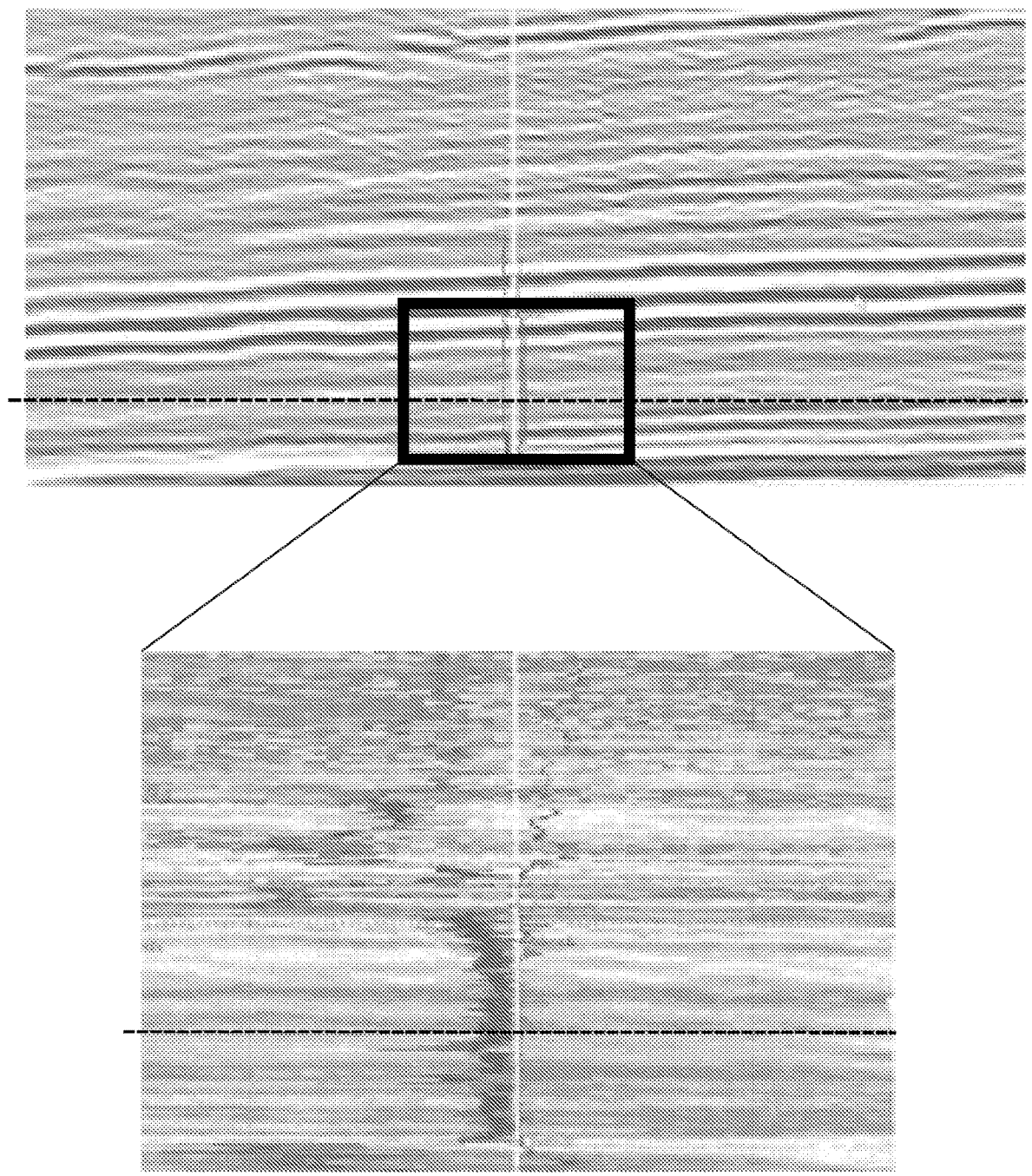
FIG. 13 illustrates images of a seismic survey of a portion of the Eagle Ford formation using inversion information and display formats including an Extended Visual Dynamic Range color display format.

A more contemporary formation of interest, especially for what is considered unconventional exploration is the Eagle Ford formation. In this case the hydrocarbon production is sought within the source rock itself which while filled with hydrocarbons has rock properties often unfavorable for to establishing commercial production. With these newer tools at hand for imaging from discrete Wavefield captures, even here we achieve remarkable visibility, especially in regard to resolution within that formation. When we compare the holographic Image using a standard display with the EVDR color display scaled in Velocity, with color changes representing velocity changes of 400 ft/see, we clearly see detail which most often can be related to production capability (FIG. 13). Most important here also is understanding that images can often be transformed to further represent estimates of physical information we desire, and also presented with quantitative measures.

Application of Data

In the prior disclosure, two concepts were introduced where additional discussion was needed, but deferred, inversion, and the Extended Visual Dynamic Range (EVDR) color display. We now provide additional insights concerning these methods, while also emphasizing the more general practical needs from imaging which they directly address. Inversion provides for one family of imaging applications a "gateway" from the rather abstract appearance and significance of imaged wavefields to concrete estimates of physical properties such as material propagation velocities. In medical imaging a counterpart transformation might be tissue identification. EVDR is concerned with rendering greater interpretive visibility by the displays to the human eye of underlying imaging information content, as well as introducing some quantification. Such displays can be critical, particularly in applications where experience and judgement are essential to the interpretation.

Simple inversion theory by R. O. Lindseth shows that for the seismic exploration data illustrations, a procedure of mathematical integration of the wavefield image reflection data over the time coordinate, transforms them to represent in a qualitative sense, the propagation velocities as had been encountered (see Geophysics, Vol. 44, No. 1, 1979, pp. 3-26). Such information is limited in its time frequency content to frequencies perhaps above 4 or 5 Hz owing to the physics of the data capture. Very low frequency information components are very difficult to include. We can develop direct information for such frequencies (in a limited manner) from measurements in boreholes of formation velocities, or also by measuring averaged velocities from the data capture using geometric elements of the signal propagation.

With more complete (but also limited) descriptions of the propagation velocities we can apply empirical and statistical methods to transform the captured wavefield data to approximations of the propagation velocities. Such methods can often produce quite good estimates of the propagation velocities and are generically known as Inversions. Still other methods for obtaining such information also exist, as for example those known as full waveform inversions (FWI). The image of the Eagle Ford formation shown in FIG. 13 presents such Inversion information, but also using an EVDR Color display which was also just explained.

Sources and receivers may be interchanged for many imaging applications. Procedures in those applications may relate to data capture decimations. Decimations can lower costs and reduce survey completion times. They also decrease signal-to-noise-levels. Performing decimations involving cost relationships of sources and receivers may affect values of IQ and/or ratio M.

When we have a data capture and subsequent Imaging with a given value of ratio M, we do not know at all, the full details of the data acquisition activity including costs, timing, operational issues, etc. Sources may sometimes be more expensive than receivers. This can be true for exploration seismic surveys, but also for x-rays and ultrasound, where expense can also translate to energy limits. In marine seismic surveys sources are cheap and can be discharged rapidly. Hence, when we contemplate or plan any Imaging project which will employ discrete methods, the requirements and limitations must be carefully thought out. The joint use and coordination of all elements will define costs, execution time, ratio M and IQ values, as well as incorporating and including all necessary constraints. A reasonable approach should address all the steps and seek a solution which approaches some optimum according to defined criteria.

Reasonable studies to better understand the processes in concert may be made starting with existing fully executed procedures, which have employed methods regarded as standard, but now testing data reconfigurations, decimations and imaging variations, to suggest approaches to optimization in terms of cost, timing, equipment utilization, energy volume, and any other factors of relevance. Determining practical limits as described will likely not provide precise or fully optimized results, but better results for future applications. We may think of such approaches as simulated "field testing".

What is claimed as the invention is:

1. A method of digital imaging of living tissue, comprising:
    obtaining wavefield data representing recordings of a propagating wavefield through living tissue;
    obtaining a reference digital image of a portion or all of the living tissue generated from the wavefield data;
    selecting a holographic computational method of imaging the wavefield data;
    selecting a data subset from the wavefield data;
    decimating the data subset; and
    generating a new digital image based on the selected holographic computational method of imaging and the decimated data subset.

2. The method of claim 1, wherein the holographic computational method of imaging the wavefield data is from a group consisting of the Kirchhoff diffraction stacking method, the Kirchhoff wave front "smear" method, wavefield synthesis, and wave equation-based methods.

3. The method of claim 1, wherein selecting the data subset from the wavefield data is based on one or more parameters selected from the group consisting of field sampling, imaging sampling, and image quality.

4. The method of claim 1, further comprising calculating a sampling ratio by dividing a number of data samples in the data subset by a number of image samples in the data subset.

5. The method of claim 1, wherein the decimated data subset represents a sampling ratio less than a reference sampling ratio of the reference digital image.

6. The method of claim 1, wherein the new digital image has a new image quality value greater than a reference image quality value of the reference digital image.

7. The method of claim 1, wherein generating the new digital image is also based on one or more parameters corresponding to the data subset selected from the group consisting of legal parameters, operational parameters, financial parameters, and safety parameters.

8. The method of claim 1, further comprising determining a quantitative difference measure between the reference digital image and the new digital image.

9. The method of claim 1, wherein determining the quantitative difference measure between the reference digital image and the new digital image is based on the changing of one or more parameters selected from the group consisting of field sampling, imaging sampling, and image quality.

10. The method of claim 1, further comprising implementing an imaging survey on another propagation volume based on a configuration of source array and receiver array corresponding to the data subset.

11. A method of digital imaging of living tissue, comprising:
    obtaining wavefield data representing recordings of a propagating wavefield through living tissue;
    obtaining a reference digital image of a portion or all of the living tissue generated from the wavefield data, wherein the reference image has a reference sampling ratio;
    selecting a holographic computational method of imaging the wavefield data;
    selecting a data subset from the wavefield data;

decimating the data subset, wherein the decimated data subset represents a sampling ratio less than the reference sampling ratio; and generating a new digital image based on the selected holographic computational method of imaging and the decimated data subset, wherein the new digital image has a new image quality value greater than the reference image quality value.

12. The method of claim 11, further comprising calculating a sampling ratio by dividing a number of data samples in the data subset by a number of image samples in the data subset.

13. The method of claim 11, further comprising determining a quantitative difference measure between the reference digital image and the new digital image.

14. The method of claim 11, further comprising determining a quantitative difference measure between the reference digital image and the new digital image based on the changing of one or more parameters selected from the group consisting of field sampling, imaging sampling, and image quality.

15. A method of digital imaging of living tissue, comprising:

obtaining wavefield data representing recordings of a propagating wavefield through living tissue;

obtaining a reference digital image of a portion or all of the living tissue generated from the wavefield data, wherein the reference image has a reference image quality value;

selecting a holographic computational method of imaging the wavefield data;

selecting a data subset from the wavefield data;

decimating the data subset; and generating a new digital image based on the selected holographic computational method of imaging and the decimated data subset, wherein the new digital image has a new image quality value greater than the reference image quality value.

16. The method of claim 15, wherein selecting the data subset from the wavefield data is based on one or more parameters selected from the group consisting of field sampling, imaging sampling, and image quality.

17. The method of claim 15, wherein the decimated data subset represents a sampling ratio less than a reference sampling ratio of the reference digital image.

18. The method of claim 15, further comprising determining a quantitative difference measure between the reference digital image and the new digital image based on the changing of one or more parameters selected from the group consisting of field sampling, imaging sampling, and image quality.

19. The method of claim 15, further comprising determining a quantitative difference measure between the reference digital image and the new digital image.

* * * * *